United States Patent
Romo et al.

(10) Patent No.: US 10,889,596 B2
(45) Date of Patent: Jan. 12, 2021

(54) BETA-AMINO PATEAMINE A DERIVATIVES AND METHODS FOR TREATING CHRONIC LYMPHOCYTIC LEUKEMIA

(71) Applicant: The Texas A&M University System, College Station, TX (US)

(72) Inventors: Daniel Romo, Waco, TX (US); Kenneth G. Hull, College Station, TX (US); Mingzhao Zhu, Eddy, TX (US); Omar Robles, Redwood City, CA (US)

(73) Assignee: The Texas A&M University System, College Station, TX (US)

( * ) Notice: Subject to any disclaimer, the term of this patent is extended or adjusted under 35 U.S.C. 154(b) by 41 days.

(21) Appl. No.: 16/090,528

(22) PCT Filed: Mar. 31, 2017

(86) PCT No.: PCT/US2017/025448
§ 371 (c)(1),
(2) Date: Oct. 1, 2018

(87) PCT Pub. No.: WO2017/173313
PCT Pub. Date: Oct. 5, 2017

(65) Prior Publication Data
US 2019/0177339 A1    Jun. 13, 2019

Related U.S. Application Data

(60) Provisional application No. 62/316,299, filed on Mar. 31, 2016.

(51) Int. Cl.
*C07D 513/08* (2006.01)
*A61K 47/68* (2017.01)
(Continued)

(52) U.S. Cl.
CPC .......... *C07D 513/08* (2013.01); *A61K 31/429* (2013.01); *A61K 47/6803* (2017.08); *A61P 35/02* (2018.01)

(58) Field of Classification Search
None
See application file for complete search history.

(56) References Cited

U.S. PATENT DOCUMENTS 7,230,021 B2    6/2007  Romo et al.
8,841,285 B2    9/2014  Romo et al.
(Continued)

FOREIGN PATENT DOCUMENTS

EP      0647645 A1      4/1995
WO    2003077862    *   9/2003
WO    2013152299 A2   10/2013

OTHER PUBLICATIONS

Romo et al. ("Romo", J. Am. Chem. Soc.. 2004, 126, 10582-10588) (Year: 2004).*
(Continued)

*Primary Examiner* — Karl J Puttlitz
(74) *Attorney, Agent, or Firm* — Christensen O'Connor Johnson Kindness

(57) ABSTRACT

Pateamine A derivatives, pharmaceutical compositions that include the derivatives, and methods for treating chronic lymphocytic leukemia using the derivatives.

34 Claims, 12 Drawing Sheets

(51) Int. Cl.
*A61P 35/02* (2006.01)
*A61K 31/429* (2006.01)

(56) References Cited

U.S. PATENT DOCUMENTS

2003/0216436 A1 11/2003 Romo et al.
2013/0053994 A1 2/2013 Rensch et al.

OTHER PUBLICATIONS

Rzasa et al., Journal of the American Chemical Society (1998), 120(3), 591-592 (Year: 1998).*
Romo et al., Journal of the American Chemical Society (1998), 120(47), 12237-12254 (Year: 1998).*
Remuinan et al., Tetrahedron Letters (2000), 41(38), 7367-7371 (Year: 2000).*
Extended European Search Report dated Sep. 6, 2019, issued in corresponding European Application No. 17776804.1, filed Mar. 31, 2017, 8 pages.
Low, W.-K., et al., "Second-Generation Derivatives of the Eukaryotic Translation Initiation Inhibitor Pateamine A Targeting elF4A as Potential Anticancer Agents," Bioorganic & Medicinal Chemistry 22(1):116-125, Jan. 2014.
Polakis, P., "Antibody Drug Conjugates for Cancer Therapy," Pharmacological Reviews 68(1):3-19, Jan. 2016.
International Search Report and Written Opinion dated Jun. 20, 2016, issued in corresponding International Application No. PCT/US16/25355, filed Mar. 31, 2016, 10 pages.
International Search Report and Written Opinion dated Jun. 22, 2017, issued in related International Application No. PCT/US2017/025448, filed Mar. 31, 2017, 7 pages.
International Preliminary Report on Patentability dated Oct. 3, 2017, issued in corresponding International Application No. PCT/US2016/025355, filed Mar. 31, 2016, 8 pages.
International Preliminary Report on Patentability dated Oct. 2, 2018, issued in corresponding International Application No. PCT/US2017/025448, filed Mar. 31, 2017, 5 pages.
European Examination Report dated Jun. 29, 2020, issued in corresponding European Application No. 17776804.1, filed Mar. 31, 2017, 3 pages.

* cited by examiner

| Compound | IC50, μM | | Human plasma protein binding | | FBS protein binding | |
|---|---|---|---|---|---|---|
| | Plasma | FBS | Fraction Bound (%) | Recovery (%) | Fraction Bound (%) | Recovery (%) |
| PxA | 0.20 | 0.20 | 97.2 | 69.0 | 98.2 | 83.0 |
| OR-IV-234 | 0.35 | 0.33 | 86.4 | 54.0 | | |
| DMDAPxA | 0.42 | 0.65 | 99.7 | 31.4 | 99.1 | 70.3 |

*Fig. 7B.*

BETA-AMINO PATEAMINE A DERIVATIVES AND METHODS FOR TREATING CHRONIC LYMPHOCYTIC LEUKEMIA

CROSS-REFERENCES TO RELATED APPLICATIONS

This application is the national stage of PCT/US2017/025448, filed Mar. 31, 2017, which claims the benefit of Application No. 62/316,299, filed Mar. 31, 2016, each application is expressly incorporated herein by reference in its entirety.

FIELD OF THE INVENTION

The present invention relates to β-amino pateamine A derivatives and methods for treating chronic lymphocytic leukemia using the β-amino pateamine A derivatives.

BACKGROUND OF THE INVENTION

Effective new cancer therapies have been developed based on agents with novel mechanisms of action that specifically target the pathophysiology of malignances. Most of these diseases exhibit a pronounced defect in normal lymphocyte cell death mechanisms due to overexpression of pro-survival proteins. It is now recognized that a critical aspect of B cell malignancy metabolism is directed at replenishing the pro-survival proteins that keep these cells from dying due to apoptosis. This is required because sequence motifs intrinsic to the primary protein structure of these pro-survival proteins, signal for the rapid turnover of these proteins (e.g. Mcl-1, XIAP). This is a hallmark of the pathophysiology of B cell malignancies. Importantly, even transient inhibition of translation rapidly diminishes these key proteins to a level that cannot prevent apoptosis. Once initiated, this lethal process is irreversible. Because normal lymphoid cells do not exhibit this dependency, it appears that CLL cells are "addicted" to the continual expression of the anti-apoptotic proteins for survival.

Pateamine A (PatA) was initially isolated from the marine sponge *Mycale* sp. by bioassay-guided fractionation based on its cytotoxic activity against P388 murine leukemia cells ($IC_{50}$, 0.27 nmol/L). Consistent with its cytotoxicity, PatA was subsequently shown to induce apoptosis in several cancer cell lines. Des-methyl, des-amino Pateamine A (DMDAPatA) is a simplified analog of the natural product that is easier to synthesize and a potent anti-proliferative agent in vitro against >30 human cancer cell lines.

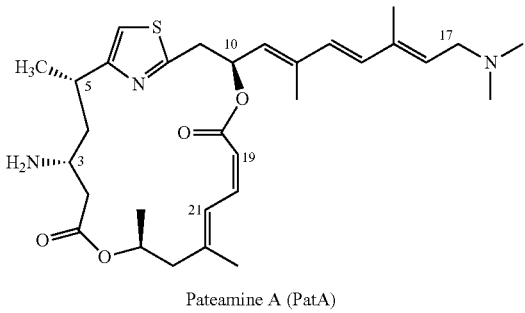

Pateamine A (PatA)

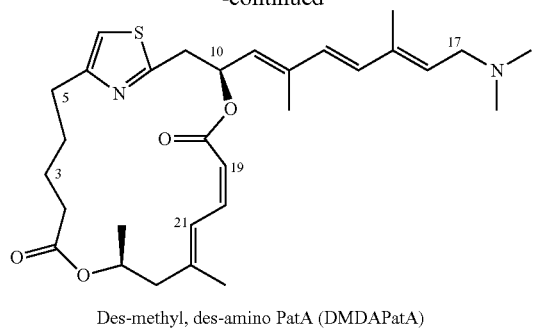

Des-methyl, des-amino PatA (DMDAPatA)

PatA and DMDAPatA inhibit cap-dependent translation initiation by sequestration of eIF4A that prevents formation of the eIF4F complex, or by stalling the initiation complex on mRNA. Xenograft studies in mice showed DMDAPatA has high activity in models of human leukemia and melanoma leading to significant tumor reduction, thus demonstrating good bioavailability. The synthesis of >20 derivatives of PatA led to the identification of DMDAPatA which was also found to be significantly more stable than the natural product. Overexpression of multidrug resistant protein did not affect this activity. Importantly, DMDAPatA reduces the levels of intrinsically short-lived anti-apoptotic proteins in primary CLL cells, and initiates apoptosis. However, preliminary data on DMDAPatA suggests that it is highly protein bound in human plasma and may lack sufficient in vivo potency required for development as an effective therapeutic agent.

Although PatA and DMDAPatA appear to be attractive candidates for the development of therapeutic agents, a need exists for improved PatA derivatives having therapeutic effectiveness, low toxicity, and advantageous pharmacokinetic properties. The present invention seeks to fulfill these needs and provides further related advantages.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIGS. 7A and 7B compare primary CLL cell potency and plasma protein binding for a representative pateamine A derivative (OR-IV-234) with PatA and DMDAPatA as controls for CLL cells cultured in media supplemented with either 10% FBS or patient plasma. Percent survival as a function of derivative concentration is shown in FIG. 7A. $IC_{50}$ and protein binding results are summarized in FIG. 7B.

DETAILED DESCRIPTION OF THE INVENTION

Figure 1:
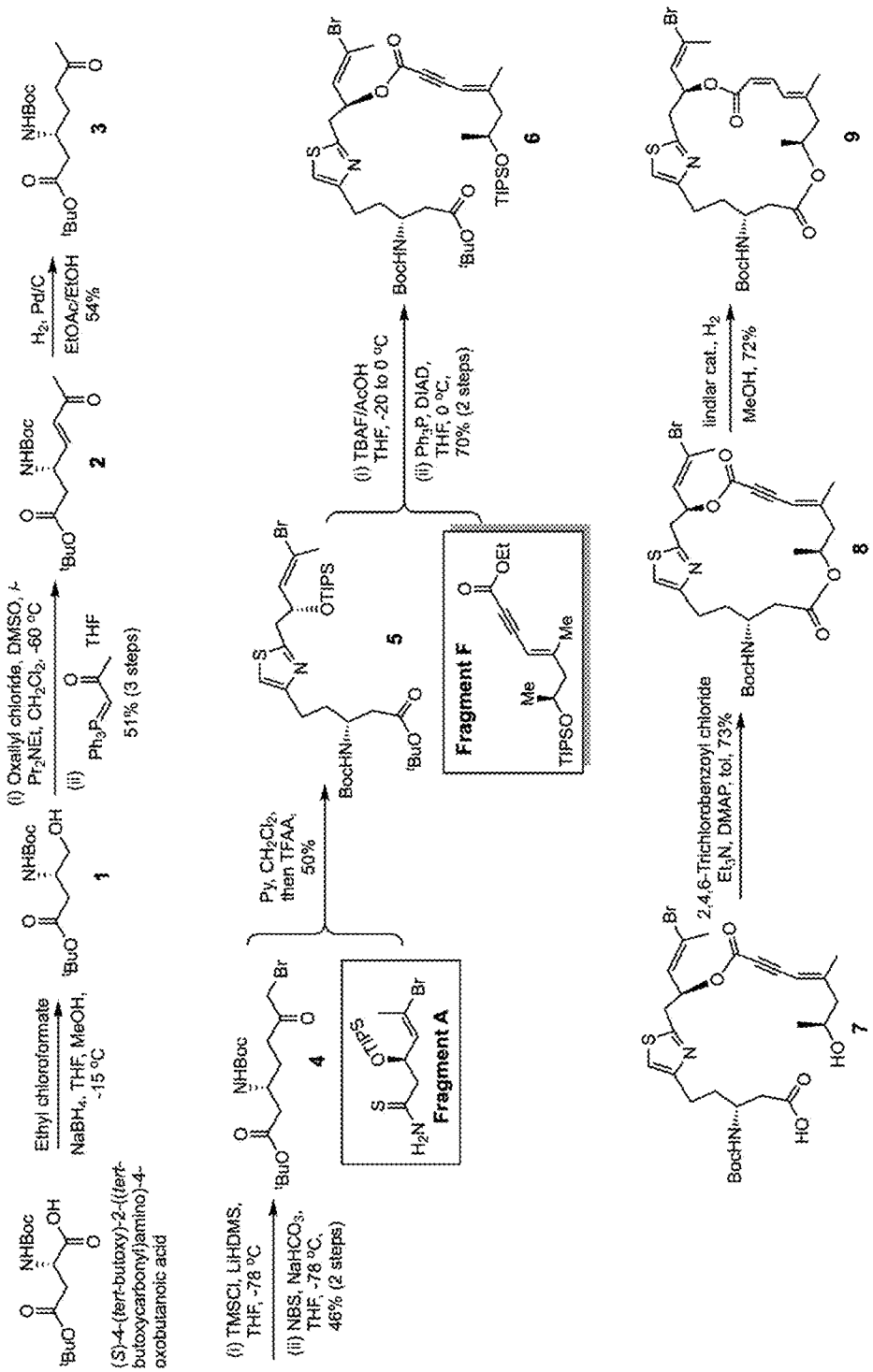
FIG. 1 is a schematic illustration of the preparation of a synthetic intermediate useful in the preparation of representative β-amino pateamine A amide derivatives of the invention.

The present invention provides β-amino pateamine A derivatives, pharmaceutical compositions that include the derivatives, and methods for using the derivatives. The compounds of the invention are simplified analogs of pateamine A that lack the C5-methyl group. The compounds of the invention are β-amino β-amino) pateamine A derivatives.

The compounds of the invention are derivatives of the translation inhibitor pateamine A and as pateamine A derivatives, the compounds of the invention are expected to provide anticancer and antiproliferative effects by inhibition of eIF4A-dependent translation initiation.

The compounds of the invention display potent inhibitory activity against chronic lymphocytic leukemia (CLL) cells and lower plasma protein binding (PPB) in human plasma. The combination of potency and low PPB render the compounds candidates for development of therapeutic agents for treatment of CLL.

The inhibition of translation in CLL cells has the potential for clinical development of therapies for B cell malignancies and to overcome drug resistance to existing standard of care therapeutics. Relapsed refractory CLL remains a clinical problem associated with poor overall survival. Due to their unique mode of action, inhibition of translation and protein biosynthesis, the compounds of the invention may be useful for combating resistant forms of CLL.

β-Amino Pateamine Derivatives

In one embodiment, the invention provides pateamine A derivatives having formula (I), stereoisomers, racemates, and pharmaceutically acceptable salts thereof:

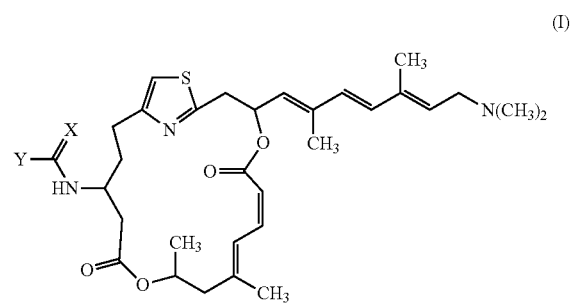

(I)

wherein

X is selected from O, NH, and S; and

Y is selected from R, $OR^1$, $SR^1$, and $N(R^1)R^2$, wherein R is selected from C1-C6 alkyl, C1-C6 haloalkyl, C6-C10 aryl, and C3-C12 alkyl groups in which one or more carbons are replaced with O or N atoms, and wherein $R^1$ and $R^2$ are independently selected from hydrogen, C1-C6 alkyl, C1-C6 haloalkyl, C6-C10 aryl, and C3-C12 alkyl groups in which one or more carbons are replaced with O or N atoms.

In certain embodiments, the invention provides pateamine A derivatives having formula (II), and racemates and pharmaceutically acceptable salts thereof:

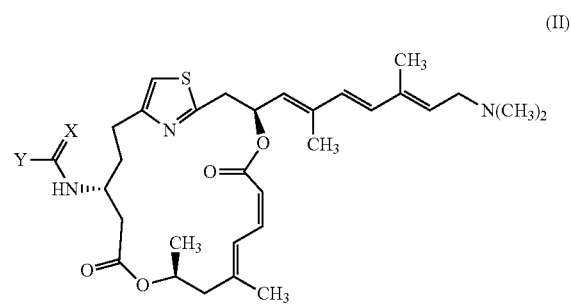

(II)

wherein X, Y, R, $R^1$, and $R^2$ are as above for formula (I).

Pharmaceutically acceptable salts may be formed from compounds of formulae (I) and (II) and a pharmaceutically acceptable organic acids (e.g., carboxylic acids) or inorganic acid (e.g., mineral acids). Representative acids include hydrochloric acid, sulfuric acid, phosphoric acid, formic acid, acetic acid, trifluoroacetic acid, maleic acid, fumaric acid, succinic acid, tartaric acid, oxalic acid, citric acid, malic acid, benzoic acid, toluenesulfonic acid, methanesulfonic acid, and benzenesulfonic acid. Such salts may be formed during or after the synthesis of the compounds of formulae (I) or (II).

Representative salts of the invention include those of formula (III):

(III)

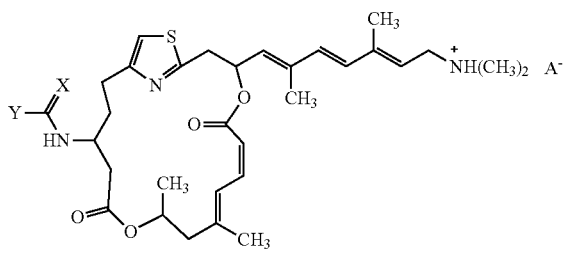

wherein X and Y are as described above for formulae (I) and (II), and A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

In one embodiment, representative salts of the invention have formula (IV):

(IV)

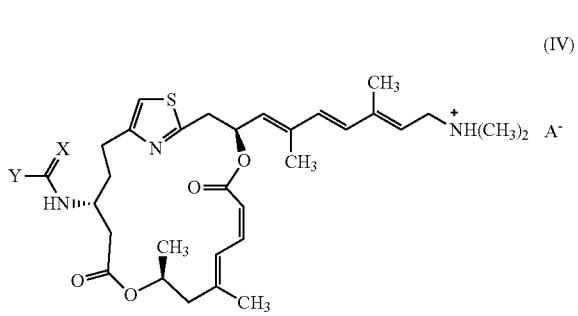

wherein X and Y are as described above for formulae (I) and (II), and A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

For compounds of formulae (I), (II), (III), and (IV), C1-C6 alkyl groups include straight chain (i.e., methyl, ethyl, n-propyl, n-butyl, n-pentyl, and n-hexyl), branched (e.g., s-propyl, s-butyl, t-butyl, s-pentyl, and s-hexyl), and cycloalkyl (i.e., cyclopropyl, cyclobutyl, cyclopentyl, and cyclohexyl) group;

C1-C6 haloalkyl groups include C1-C6 alkyl groups further substituted with one or more halo (e.g., fluoro or chloro) groups (e.g., trifluoromethyl or trichloromethyl);

C6-C10 aryl groups include phenyl groups optionally substituted with one of more alkyl groups (e.g., methyl, ethyl);

C3-C12 alkyl groups refer to C3-C12 alkyl groups in which one or more carbons are replaced with O or N atoms include ether-containing groups and amine-containing groups that may impart increased water solubility to the compounds. Representative ether-containing groups include —CH$_2$—O—CH$_3$, —CH$_2$CH$_2$—O—CH$_3$, and —CH$_2$CH$_2$—O—CH$_2$CH$_2$—O—CH$_3$. Representative amine-containing groups include —CH$_2$—NH—CH$_3$, —CH$_2$—N(CH$_3$)$_2$, —CH$_2$CH$_2$—NH—CH$_3$, and —CH$_2$CH$_2$—N(CH$_3$)$_2$.

The invention provides compounds of formulae (I), (II), (III), and (IV) include the following embodiments:

X is O and Y is R (amides), in certain of these embodiments, R is methyl, trifluoromethyl, or t-butyl;

X is O and Y is OR$^1$ (carbamates), in certain of these embodiments, R$^1$ is methyl or t-butyl;

X is O and Y is N(R$^1$)R$^2$ (ureas), in certain of these embodiments, R$^1$ is hydrogen and R$^2$ is hydrogen, or R$^1$ is hydrogen and R$^2$ is methyl;

X is O and Y is SR$^1$, in certain of these embodiments, R$^1$ is methyl or t-butyl;

X is S and Y is R (thioamides), in certain of these embodiments, R is methyl;

X is S and Y is OR$^1$ (thiocarbamates), in certain of these embodiments, R$^1$ is methyl or t-butyl;

X is S and Y is N(R$^1$)R$^2$ (thioureas), in certain of these embodiments, R$^1$ is hydrogen and R$^2$ is hydrogen, or R$^1$ is hydrogen and R$^2$ is methyl;

X is S and Y is SR$^1$, in certain of these embodiments, R$^1$ is methyl or t-butyl;

X is NH and Y is R, in certain of these embodiments, R is methyl, trifluoromethyl, or t-butyl;

X is NH and Y is OR$^1$, in certain of these embodiments, R$^1$ is methyl or t-butyl;

X is NH and Y is N(R$^1$)R$^2$, in certain of these embodiments, R$^1$ is hydrogen and R$^2$ is hydrogen, or R$^1$ is hydrogen and R$^2$ is methyl; and X is NH and Y is SR$^1$, in certain of these embodiments, R$^1$ is methyl or t-butyl.

Figure 2:
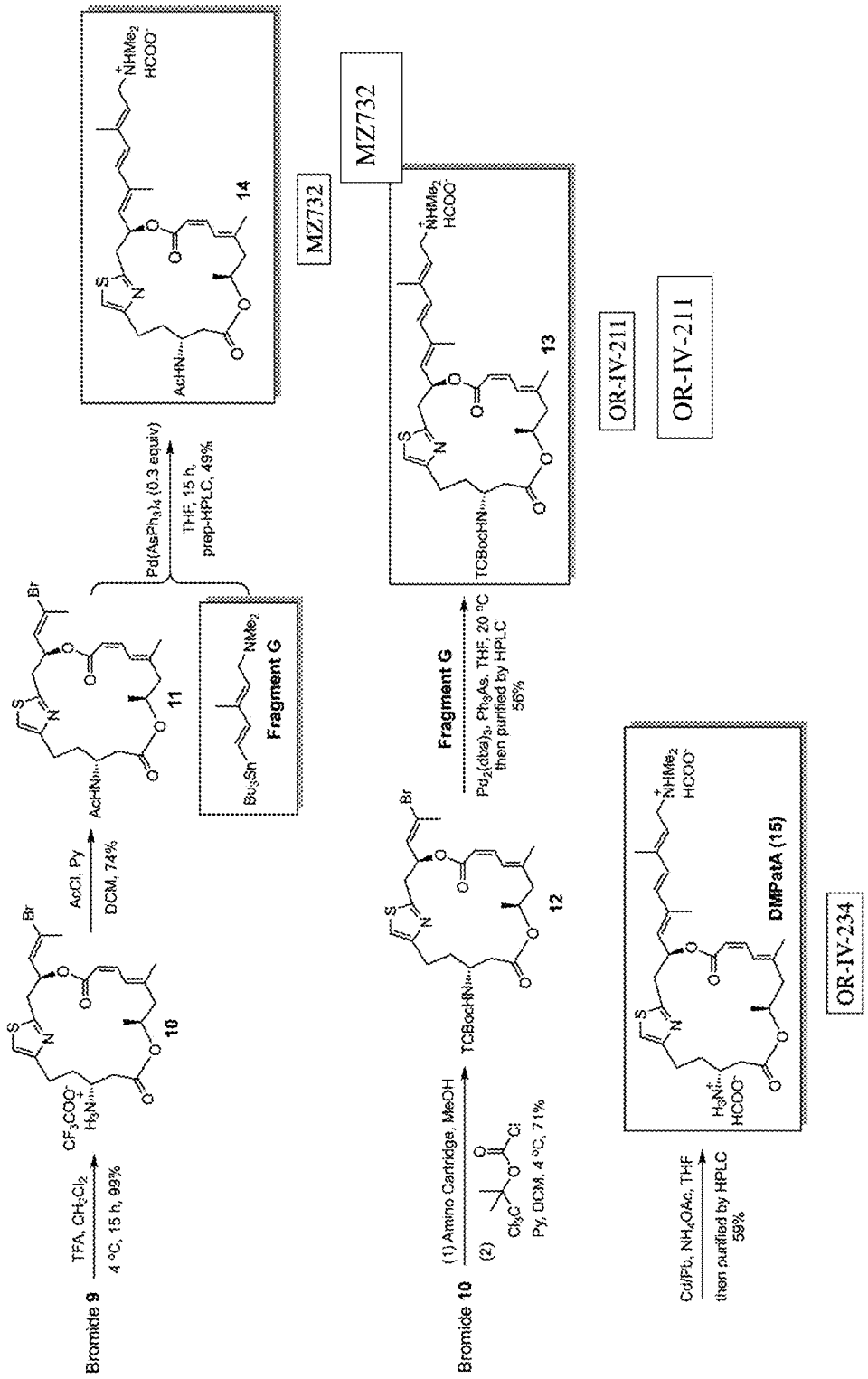
FIG. 2 is a schematic illustration of the preparation of representative β-amino pateamine A amide derivatives of the invention.

The preparation of representative β-amino pateamine A amide derivatives of the invention is described in Example 1 and illustrated in FIG. 1 (preparation of synthetic intermediate 9) and FIG. 2 (preparation of representative β-amino pateamine A amide derivatives 13 (OR-IV-211), 14 (MZ732), and 15 (OR-IV-234).

In another embodiment, the invention provides pateamine A derivatives having formula (V), stereoisomers, racemates, and pharmaceutically acceptable salts thereof:

(V)

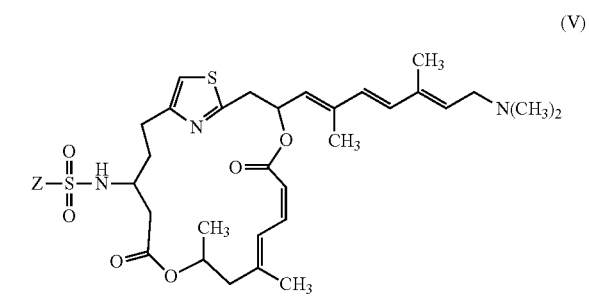

wherein

Z is selected from R and OR$^1$, wherein R and R$^1$ are as described above for formulae (I)-(IV).

In certain embodiments, the invention provides pateamine A derivatives having formula (VI), and racemates and pharmaceutically acceptable salts thereof:

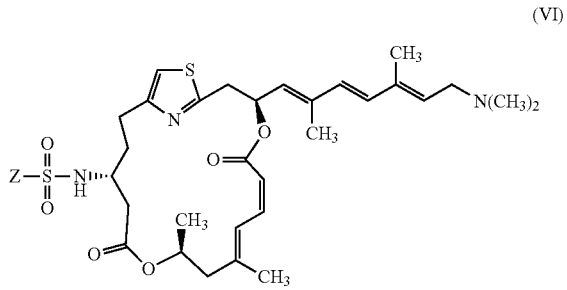
(VI)

wherein Z is as described above for formula (V).

Representative salts of the invention include those having formula (VII):

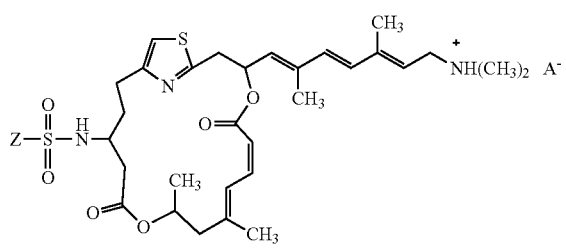
(VII)

wherein Z is as described above for formulae (V) and A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

In one embodiment, representative salts of the invention have formula (VIII):

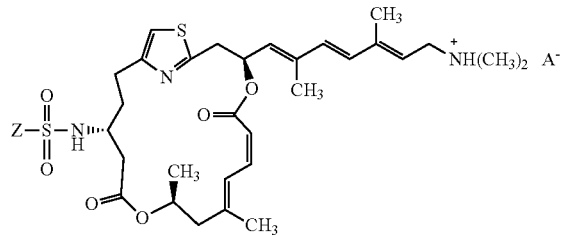
(VIII)

wherein Z is as described above for formula (V) and A⁻ is as described above for formula (VII).

The invention provides compounds of formulae (V), (VI), (VII), and (VIII) include the following embodiments:

Z is C1-C6 alkyl (e.g., methyl);

Z is C1-C6 haloalkyl (e.g., trifluoromethyl);

Z is C6-C10 aryl (e.g., phenyl); and

Z is C3-C12 alkyl in which one or more carbons are replaced with O or N atoms (e.g., —CH₂—O—CH₃, —CH₂CH₂—O—CH₃, and —CH₂CH₂—O—CH₂CH₂—O—CH₃, or —CH₂—NH—CH₃, —CH₂—N(CH₃)₂, —CH₂CH₂—NH—CH₃, and —CH₂CH₂—N(CH₃)₂).

In further embodiments of the invention, pateamine A free amine derivatives, their stereoisomers, racemates, and pharmaceutical salts are provided.

In one embodiment, the invention provides pateamine A derivatives having formula (IX), and stereoisomers, racemates, and pharmaceutical salts thereof:

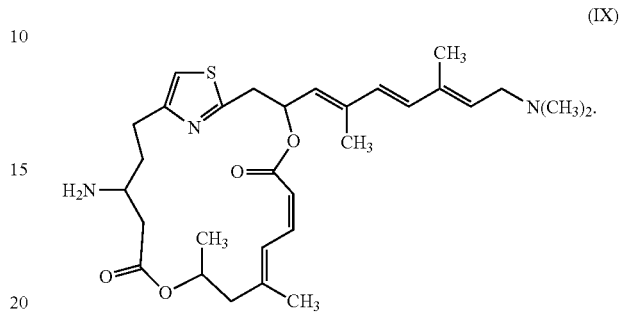
(IX)

In another embodiment, the invention provides pateamine A derivatives having formula (X), and racemates and pharmaceutically salts thereof:

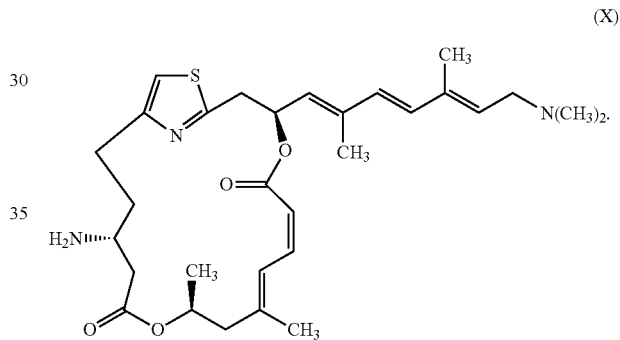
(X)

Representative free amine salts of the invention include those having formula (XI):

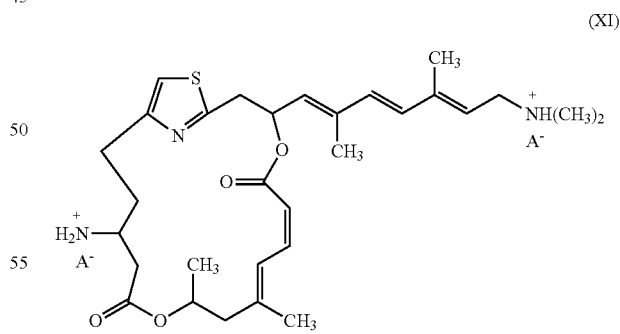
(XI)

wherein A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate. In one embodiment, A⁻ is formate.

In one embodiment, representative salts of the invention have formula (XII):

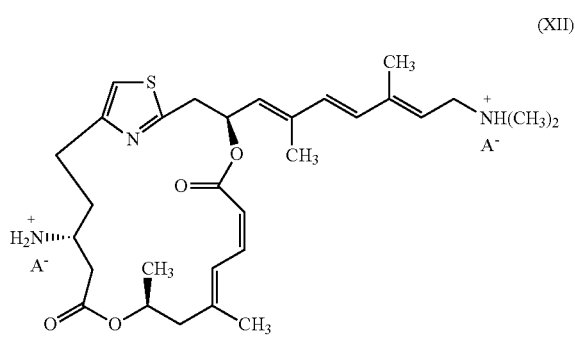

(XII)

wherein A⁻ is a pharmaceutically acceptable counter ion. Suitable counter ions include chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate. In one embodiment, A⁻ is formate.

The β-amino pateamine derivatives of the invention (i.e. compounds of formulae (I)-(VIII)) can be prepared by reacting the 3-amino group (i.e., β-amino group) of the macrocycle with a suitably reactive reagent (e.g., N-acylating or N-sulfonating reagent) to provide a variety of β-amino pateamine derivatives.

The β-amino pateamine free amine derivatives of the invention (i.e. compounds of formulae (IX)-(XII)) can be prepared by as described in Example 1.

Antibody Conjugates

In another aspect, the invention provides antibody drug conjugates for the delivery of the β-amino pateamine derivatives of the invention. The antibody drug conjugates are readily prepared from the β-amino pateamine derivatives by conjugation chemistry known in the art. In certain embodiments, the β-amino pateamine derivatives are conjugated to the antibody through the 3-amino group (i.e., β-amino group). In certain embodiments, the β-amino pateamine derivatives are conjugated to the antibody directly. In other embodiments, the β-amino pateamine derivatives are conjugated to the antibody through a linker unit.

In certain embodiments, the antibody drug conjugate is an Antibody-Linker-Drug conjugate of the formula: Ab-(LU-D)$_p$ or a pharmaceutically acceptable salt or solvate thereof wherein Ab is an antibody unit, LU is a linker unit, D is a drug unit, and p is an integer from 1 to about 20. For the antibody drug conjugates, D includes a β-amino pateamine derivative of the invention. Suitable linker units for antibody drug conjugates are known to those of skill in the art.

Suitable antibodies include, for example, monoclonal antibodies, such as chimeric, humanized or human antibodies or an antigen-binding fragment thereof. In some embodiments, the antibody unit comprises an antigen-binding region that binds to a target antigen.

In some embodiments, a substantial amount of the drug unit is not cleaved from the conjugate until the conjugate enters a cell with a cell-surface receptor specific for the antibody unit, and the drug unit is cleaved from the antibody unit when the conjugate enters the cell. In some embodiments, a substantial amount of the linker-drug unit is not cleaved from the conjugate until the conjugate enters a cell with a cell-surface receptor specific for the antibody unit, and the linker-drug unit is cleaved from the antibody unit when the conjugate enters the cell.

The term "antibody" as used herein, refers to a full-length immunoglobulin molecule or an immunologically active portion of a full-length immunoglobulin molecule (i.e., a molecule that contains an antigen binding site that immunospecifically binds an antigen of a target of interest or part thereof, such targets including, but not limited to, cancer cells. The antibody can be of any class (e.g., IgG, IgE, IgM, IgD, and IgA), or subclass (e.g., IgG1, IgG2, IgG3, IgG4, IgA1, and IgA2) of immunoglobulin molecule. The antibody can be derived from any species. In one aspect, the antibody is of human, murine, or rabbit origin. In another aspect, the antibody is polyclonal, monoclonal, bispecific, multispecific, human, humanized or a chimeric antibody, or an epitope-binding fragment of any of the above which immunospecifically bind to a target antigen.

The term "monoclonal antibody" as used herein refers to an antibody obtained from a population of substantially homogeneous antibodies (i.e., the individual antibodies comprising the population are identical except for possible naturally-occurring mutations that may be present in minor amounts). Monoclonal antibodies are highly specific, being directed against a single antigenic site.

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, that exhibit the desired biological activity. For example, a chimeric antibody may be derived from the variable region from a mouse antibody and the constant region from a human antibody.

An "antibody fragment" refers to a portion of an intact antibody, typically comprising the antigen-binding or variable region thereof. Examples of antibody fragments include Fab, Fab', F(ab')2, and Fv fragments; linear antibodies; single-chain antibody molecules; an scFv; an IgG ΔCH2, a minibody, a diabody, a triabody, a tetrabody, a dsFv; an sc-Fv-Fc; an (scFv)2; a fragment produced by a Fab expression library; an anti-idiotypic (anti-Id) antibody; and multispecific antibodies formed from antibody fragment(s).

An "intact" antibody is one which comprises an antigen-binding variable region as well as a light chain constant domain (CO and heavy chain constant domains, CH1, CH2 and CH3. The constant domains may be native sequence constant domains (e.g., human native sequence constant domains) or amino acid sequence variants thereof.

The term "diabodies" refers to small antibody fragments with two antigen-binding sites, which fragments comprise a variable heavy domain (VH) connected to a variable light domain (VL) in the same polypeptide chain. By using a linker that is too short to allow pairing between the two domains on the same chain, the domains are forced to pair with the complementary domains of another chain and create two antigen-binding sites.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

Useful monoclonal antibodies include, but are not limited to, human monoclonal antibodies, humanized monoclonal antibodies, antibody fragments, or chimeric (e.g., human-mouse or other species) monoclonal antibodies. Human monoclonal antibodies may be made by any of numerous techniques known in the art.

The antibody can also be a multispecific antibody, such as a bispecific antibody. Methods for making bispecific antibodies are known in the art. Traditional production of full-length bispecific antibodies is based on the coexpression of two immunoglobulin heavy chain-light chain pairs, where the two chains have different specificities. Because of the random assortment of immunoglobulin heavy and light chains, these hybridomas (quadromas) produce a potential mixture of 10 different antibody molecules.

Pharmaceutical Compositions

In another aspect, the invention provides pharmaceutical compositions that include a compound of the invention (i.e., a compound of formulae (I)-(XII)) and a pharmaceutically acceptable carrier.

The invention also provides pharmaceutical compositions that include an antibody conjugate of the invention (i.e., an antibody conjugate that delivers a compound of formulae (I)-(XII)) and a pharmaceutically acceptable carrier.

Suitable carriers include those suitable for administration to an animal (e.g., a human subject). Pharmaceutical compositions suitable for injectable use include sterile aqueous solutions (e.g., saline, dextrose) and dispersions.

The compounds and compositions of the invention can be orally administered, for example, with an inert diluent or carrier, enclosed in hard or soft shell gelatin capsule, or compressed into tablets. For oral therapeutic administration, the compounds and compositions can be combined with excipients and used in the form of ingestible tablets, buccal tables, troches, capsules, elixirs, suspensions, syrups, wafers, and the like. The amount of active compounds in such therapeutically useful compositions is such that a suitable dosage is obtained.

The compounds and compositions of the invention can be administered parenterally or intraperitoneally. Solutions of the compounds as free base or pharmacologically acceptable salts can be prepared in water suitably mixed with additives, such as surfactants. Dispersions can also be prepared in oils.

In the methods of the invention, the term "therapeutically effective amount" refers to an amount effective, at dosages and for periods of time necessary, to achieve the desired therapeutic result, such as reduced levels of rod gene expression or their protein products. A therapeutically effective amount of a compound may vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the administered compound are outweighed by the therapeutically beneficial effects.

It is to be noted that dosage values can vary with the severity of the condition to be alleviated. For any particular subject, specific dosage regimens can be adjusted over time according to the individual need and the professional judgment of the person administering or supervising the administration of the compositions. Dosage ranges set forth herein are exemplary only and do not limit the dosage ranges that can be selected by a medical practitioner. The amount of active compound in the composition can vary according to factors such as the disease state, age, sex, and weight of the subject. Dosage regimens can be adjusted to provide the optimum therapeutic response. For example, a single bolus can be administered, several divided doses can be administered over time or the dose can be proportionally reduced or increased as indicated by the exigencies of the therapeutic situation.

In the methods, the administration of the compound can be systemic administration to the subject. The term "subject" is intended to include mammalian organisms. Examples of subjects include humans and non-human mammals. In specific embodiments of the invention, the subject is a human.

The terms "administering," "contacting," or "treating" include any method of delivery of a compounds or a pharmaceutical composition comprising the compound into a subject's system.

Methods of Use

In certain embodiments, the β-amino pateamine compounds of the invention retain the advantageous potency of pateamine A (e.g., inhibitory activity against chronic lymphocytic leukemia (CLL) cells) and have improved bioavailability compared to pateamine A (e.g., lower plasma protein binding (PPB) in human plasma).

In one aspect, the invention provides a method for inhibiting growth of chronic lymphocytic leukemia (CLL) cells. In the method, growth of CLL cells is inhibited by contacting CLL cells with a β-amino pateamine compound of the invention (or an antibody conjugate of the invention, or a pharmaceutical composition of the invention comprising a β-amino pateamine compound or an antibody conjugate). In certain embodiments, the method is effective for inhibiting growth of chronic lymphocytic leukemia (CLL) cells in a subject (e.g., a human subject).

In another aspect, the invention provides a method for treating chronic lymphocytic leukemia (CLL). In the method, CLL is treated by administering an effective amount of a β-amino pateamine compound of the invention (or an antibody conjugate of the invention, or a pharmaceutical composition of the invention comprising a β-amino pateamine compound or an antibody conjugate) to a subject (e.g., a human subject) in need thereof.

Mechanism of Action of DMDAPatA in CLL

Figure 3A:
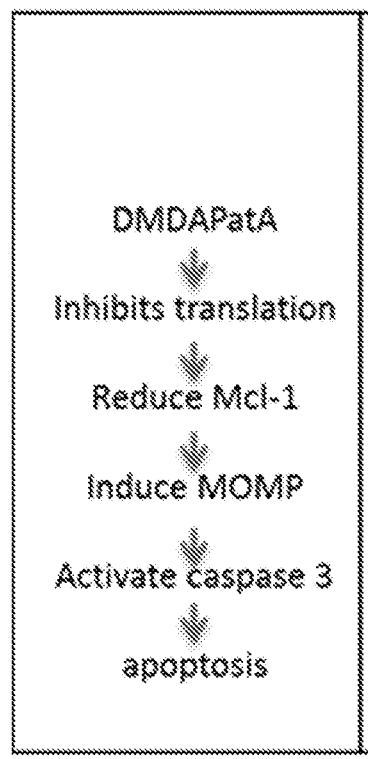
FIG. 3A is a flow diagram illustrating the mechanism of action of DMDAPatA in a study of multiple primary CLL.
Figure 3B:
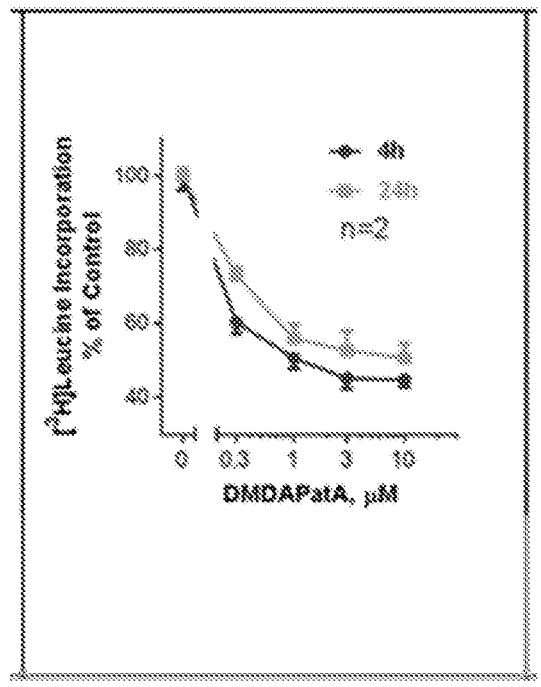
FIG. 3B shows DMDAPatA inhibition of protein synthesis as measured by [³H]leucine incorporation ([³H]leucine incorporation as percent of control as a function of DMDAPatA concentration.
Figure 3C:
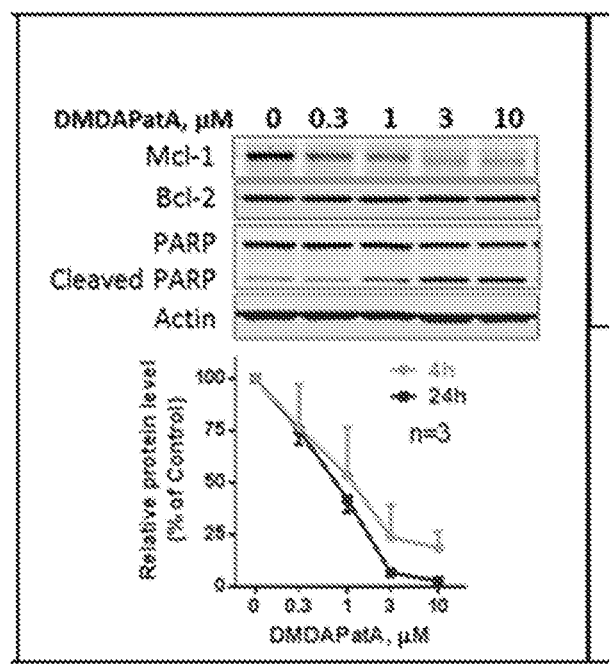
FIG. 3C shows DMDAPatA reduces the short-lived anti-apoptotic protein Mcl-1 and does not affect Bcl-2 level.
Figure 3D:
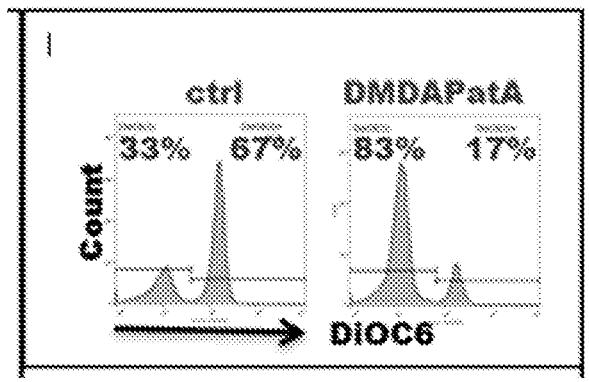
FIG. 3D shows that eliminating Mcl-1 with DMDAPatA induces mitochondrial outer membrane permeabilization (MOMP) as demonstrated by the loss of binding of the cationic dye DiOC6.
Figure 3E:
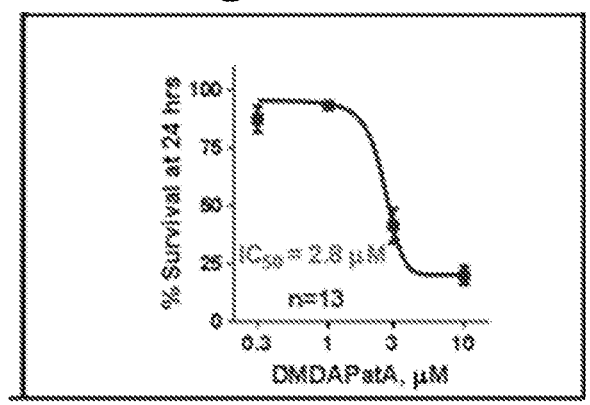
FIG. 3E compares percent CLL survival as a function of DMDAPatA concentration.

The mechanism of action of DMDAPatA was studied in multiple primary CLL samples (FIG. 3A). DMDAPatA was shown to inhibit protein synthesis as measured by [$^3$H] leucine incorporation analysis (FIG. 3B). CLL cells were incubated with DMDAPatA for 4 and 24 h then pulse labeled with [$^3$H]leucine for 1 h. The amount of [$^3$H]leucine incorporation into the acid insoluble materials (DNA, RNA and proteins) was measured by scintillation counter. These data support DMDAPatA inhibition of protein translation initiation in CLL cells. Further, DMDAPatA reduced the short-lived anti-apoptotic protein Mcl-1. This is consistent in 3 samples as quantitated in FIG. 3C. The Bcl-2 level was not affected by DMDAPatA, which is consistent with its longer half-life (FIG. 3C). Because Mcl-1 blocks apoptosis by preventing Bax and Bak from making holes on the mitochondrial membrane, eliminating Mcl-1 with DMDAPatA induced mitochondrial outer membrane permeabilization (MOMP). This was demonstrated by the loss of binding of the cationic dye DiOC6 (FIG. 3D). MOMP facilitates the release of cytochrome c from mitochondria to form the apoptosome, which activated caspase-3 and induced apoptosis. As PARP is a substrate of caspase-3, an increase of cleaved PARP in FIG. 3C indicated activation of caspase 3. Apoptosis was measured by annexin V and propodium iodide (PI) double staining followed by flow cytometry. Finally, the average $IC_{50}$ of DMDAPatA was 2.8 µM measured in 13 CLL samples (FIG. 3E).

Figure 4A:
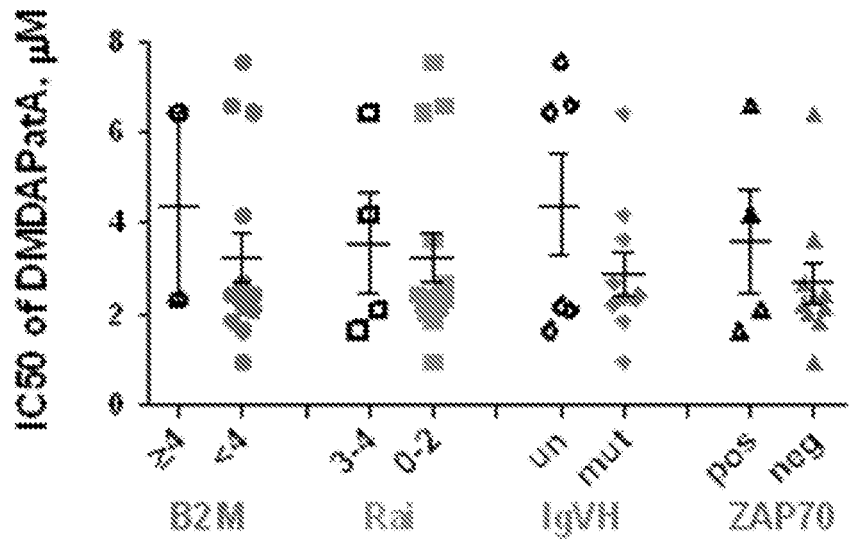
FIG. 4A compares $IC_{50}$ values of DMDAPatA (samples from CLL patients with either favorable or poor prognostic characteristics) showing no significant differences among samples in each group.

Because of the heterogeneous clinical responses of CLL patients, cellular and molecular markers have been identified to predict the disease tendency or outcome of therapy. Rai and Binet staging systems have been widely used to assess disease status and treatment options, with Rai stages III and IV considered high-risk and aggressive disease. High beta 2 macroglobulin (B2M) expression is an unfavorable prognosis to standard chemotherapy containing alkylating agents and purine nucleoside analogs. The absence of somatic mutation IgVH gene, or high expression of ZAP-70 is also associated with aggressive disease. The $IC_{50}$ values of DMDAPatA were compared in samples from CLL patients with either favorable or poor prognostic characteristics, there were no significant differences found among samples in each group (FIG. 4A). These results indicate that DMDAPatA induces apoptosis by a mechanism that is independent of these variables, suggesting that DMDAPatA may have the potential to overcome drug resistance in CLL therapy.

Figure 4B:
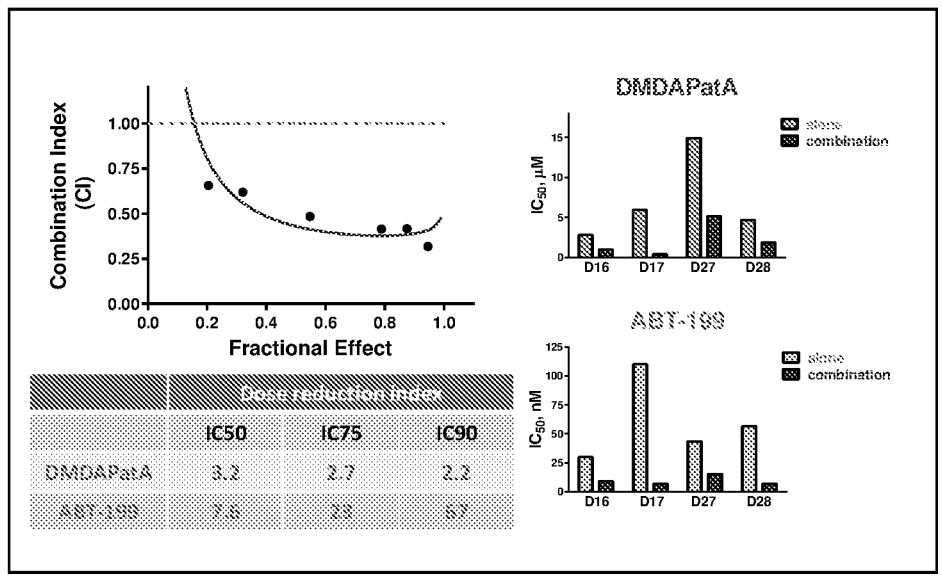
FIG. 4B shows dose reduction analysis and compares $IC_{50}$, $IC_{75}$ and $IC_{90}$ values of DMDAPatA and ABT-199, indicating mutual potentiation.

Both Bcl-2 and Mcl-1 are pro-survival proteins that regulate apoptosis by interacting with the BH3 motifs of their pro-apoptotic partners. BH3 mimetics, such as ABT-199, bind with high affinity to Bcl-2 and block this interaction, but not to Mcl-1. Resistance to BH3 mimetics is associated with upregulation of Mcl-1. Because DMDAPatA depleted Mcl-1 without affecting Bcl-2 expression, their combination should target the two parallel arms of apoptosis control and kill the CLL cells synergistically. Indeed, a median effect analysis in four CLL samples demonstrated that DMDAPatA and ABT-199 exhibited strong synergy (combination index less than 1). The dose reduction analysis showed that the combinations greatly reduced the $IC_{50}$, $IC_{75}$ and $IC_{90}$ values of each compound, indicating mutual potentiation (FIG. 4B). These results support clinical combinations of DMDAPatA and analogs with inhibitors that antagonize Bcl-2 activity.

DMDAPatA Limitations

Figure 5:
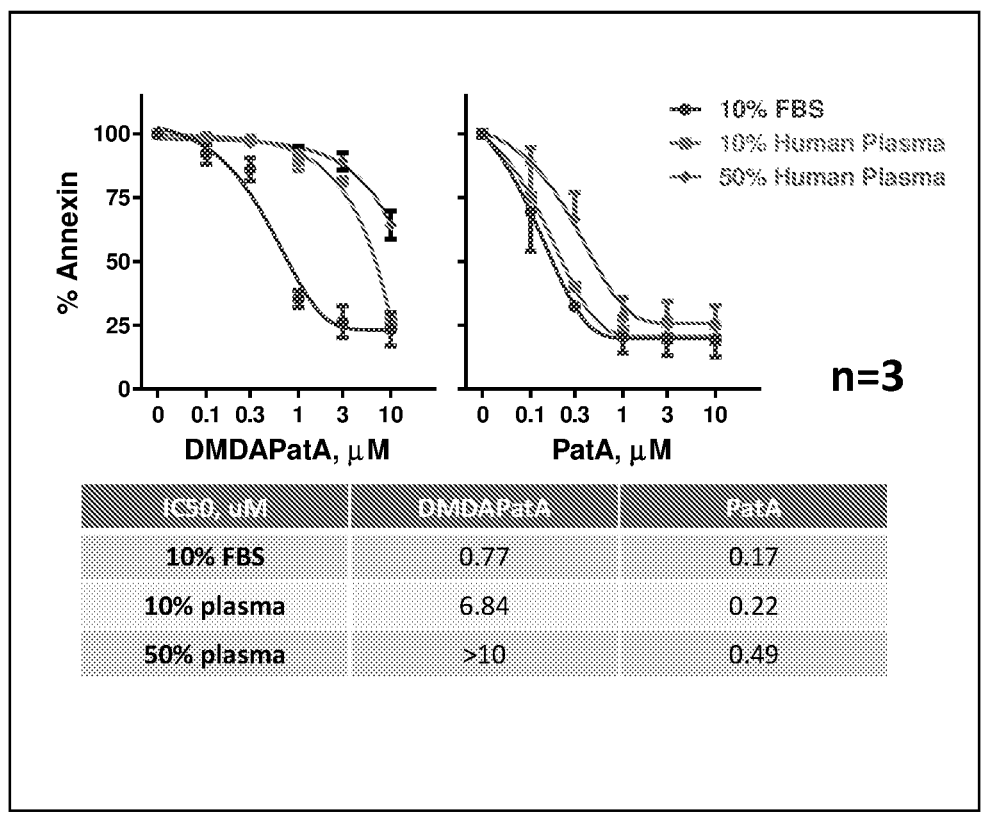
FIG. 5 compares the potency of DMDAPatA to its parental compound PatA showing that DMDAPatA was about 30 times less potent than PatA. These experiments were performed in CLL cells cultured in media supplemented with 10% patient plasma.

A direct comparison of DMDAPatA to its parental compound PatA showed that DMDAPatA was about 30 times less potent than PatA (FIG. 5). These experiments were performed in CLL cells cultured in media supplemented with 10% patient plasma. While mimicking the in vivo environment, we also found this condition beneficial in maintaining cell survival. One potential reason for the reduced potency in the presence of human plasma is stability. To test this theory, the stability of DMDAPatA was studied in FBS and human plasma at two different concentrations. Interestingly, the presence of serum greatly stabilized DMDAPatA (Table 1) and no significant difference was observed between the half-lives of DMDAPatA in FBS or human serum, excluding the plasma influence on DMDAPatA stability.

TABLE 1

| | Half-life time (hours) | |
|---|---|---|
| Testing conditions | DMDAPatA 1 uM | DMDAPatA 10 uM |
| Pure RPMI | 3 | 3.2 |
| Fetal Bovine Serum | 16 | 11.5 |
| Human Plasma | 18 | 14 |

It is well known that plasma protein binding greatly impacts drug availability and efficiency in vivo. To estimate the effect of patient plasma on the toxicity of the PatA analogs, the $IC_{50}$ of PatA and DMDAPatA were compared in RPMI media supplemented with 10% fetal bovine serum, 10% patient plasma or 50% patient plasma. The results demonstrated that increasing human plasma content in the media greatly reduced the potency of DMDAPatA, but was not as influential on Pat A, suggesting that DMDAPatA may be highly bound to patient plasma proteins (FIG. 5). Thus, synthetic efforts were directed toward the synthesis of novel analogs that are expected to have better potency and lower plasma protein binding (vide infra).

Design and Synthesis of PatA Analogs

Figure 6:
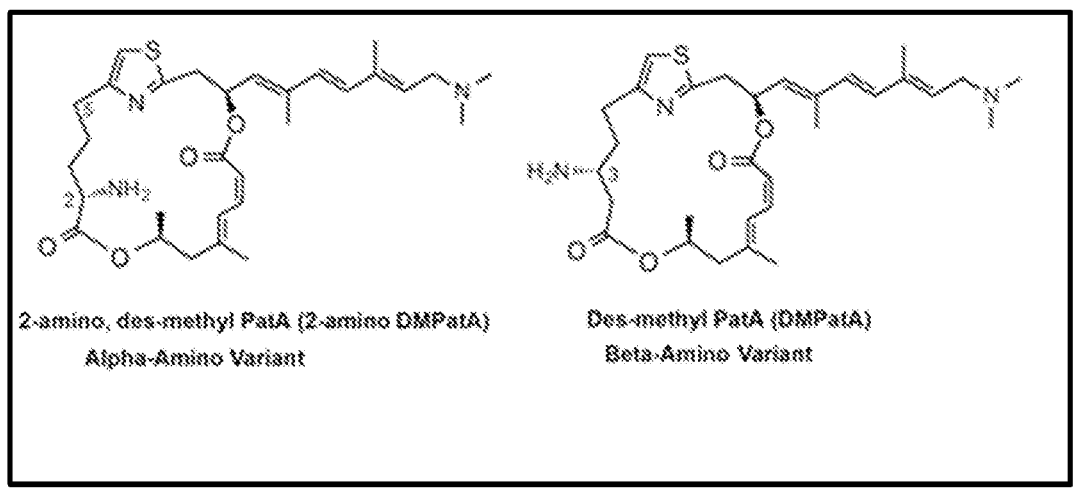
FIG. 6 compares the chemical structures of a representative α-amino (2-amino) pateamine A derivative (alpha-amino variant) and a representative β-amino (3-amino) pateamine A derivative (beta-amino variant).

A strategy to improve CLL cytotoxic potency and simultaneously lower plasma protein binding (PPB) is shown in FIG. 6. The strategy included introducing an amino group at either the C2 or C3 position of the macrocycle to improve CLL potency because the new analogs possess similar functionality as PatA, which we have shown is approximately 30 times more potent than DMDAPatA against primary CLL cells. This modification to the chemical scaffold lead to lower lipophilicity (Log D) based on calculations. Because it has been shown previously in the literature that the lipophilicity of small molecules correlates with plasma protein binding, the new amino group and other polar functionality attached to it decrease the lipophilicity of the new variants and potentially lower the PPB in human plasma. Lowering the lipophilicity of a candidate drug can also lead to other beneficial physical properties such as increased aqueous solubility. Thus, derivatives in both the alpha-amino series (2-amino, des-methyl PatA) and the beta-amino series (des-methyl PatA) are attractive from a drug design perspective.

The synthesis of the beta-amino variants des-methyl PatA (DMPatA) (OR-IV-234 or 15), MZ732 (14), and OR-IV-211 (13) are depicted (FIGS. 1 and 2). Commercially available Boc-L-aspartic acid 4-tert-butyl ester enabled the preparation of all three compounds. The longest linear sequence in the synthesis of DMPatA is also 18 steps and it is scalable for preparation of larger amounts necessary for preclinical development.

Structure-Activity Relationship (SAR) Table

The structure-activity relationship of the three beta-amino variants compared to PatA and DMDAPatA is shown in Table 2.

TABLE 2

Structure-activity relationships of derivatives.

[Structure diagram of the compound with labels E³, R¹, R², S, N, NHMe, HCOO⁻]

| Compound | Structure R¹ | R² | R³ | IC$_{50}$ (μM) 10% FBS | IC$_{50}$ (μM) 10% Plasma |
|---|---|---|---|---|---|
| PatA | NH$_2$ | H | Me | 0.20 | 0.20 |
| DMDAPaA | H | H | H | 0.65 | 6.42 |
| OR-IV-211 | NHTCBoc | H | H | 3.50 | 6.65 |
| OR-IV-234 | NH$_2$ | H | H | 0.33 | 0.35 |
| MZ732 | NHAc | H | H | 4.58 | 6.80 |

The most potent is the free amine (OR-IV-234, R¹=NH$_2$) with similar activity in FBS and human plasma. This is not surprising because structurally it is the derivative that is most comparable to PatA. Derivatives of the amine (OR-IV-211 and MZ732) with a carbamate or acetamide functional group are significantly less active than the amine itself. Thus, the free amine is the most potent analog in the beta-amino series.

Biological Screening of the PatA Analogs

Figure 7A:
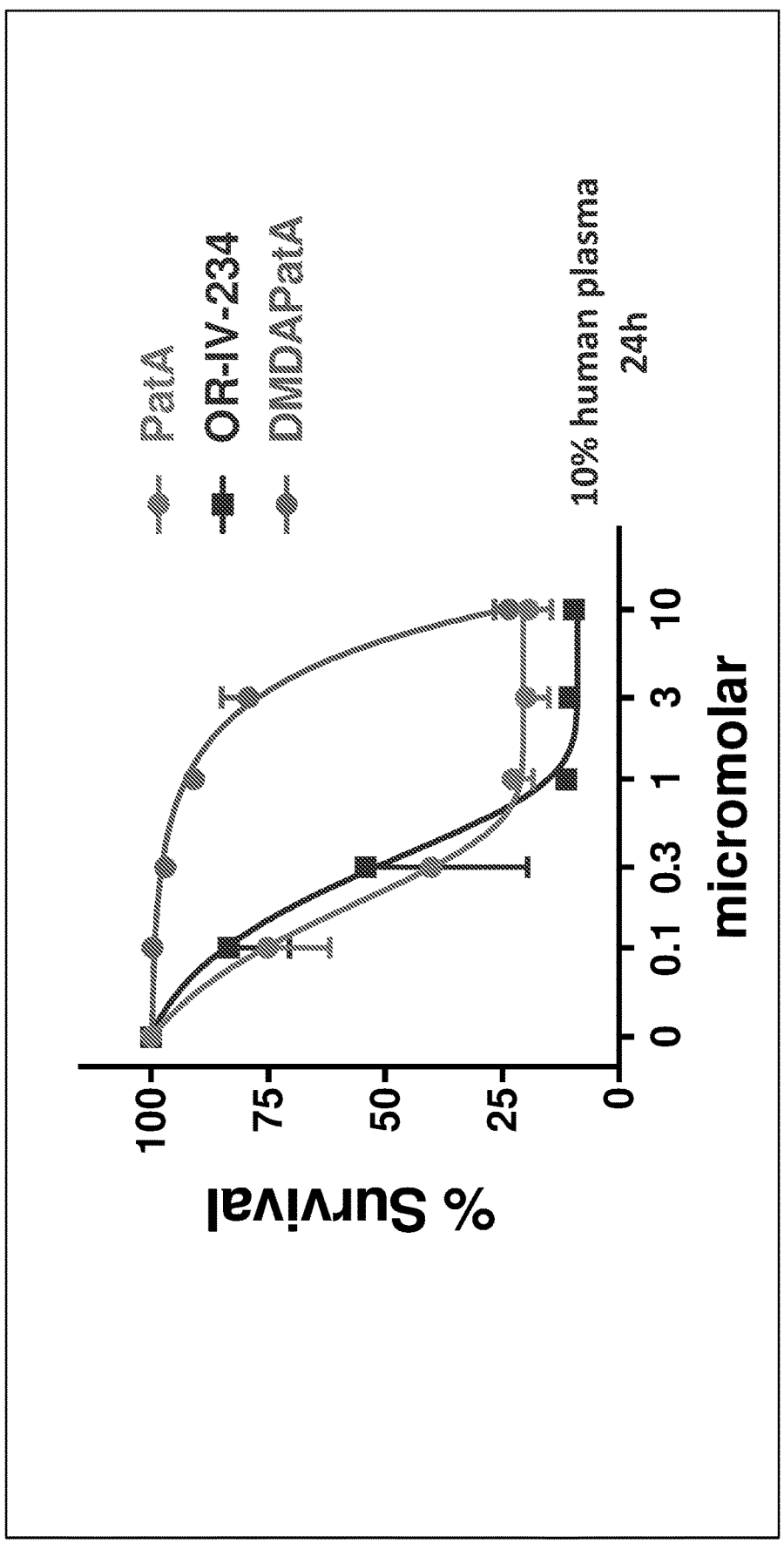

To screen for PatA analogs with greater potency and less plasma protein binding, the toxicity of the analogs to primary CLL cells was measured after 24 of incubation by annexin/PI double staining followed by flow cytometry. This was compared between CLL cells cultured in media supplemented with either 10% FBS or patient plasma to evaluate the plasma influence. Plasma protein binding was assessed using the equilibrium dialysis method (FIG. 7B). The results showed that DMDAPatA is 99.7% plasma protein bound, consistent with lower potency in plasma. The low recovery of DMDAPatA in plasma may suggest non-specific binding, poor aqueous solubility or irreversible protein binding. OR-IV-234 demonstrated much lower plasma protein binding (PPB) than both PatA and DMDAPatA with modest recovery.

Figure 8A:
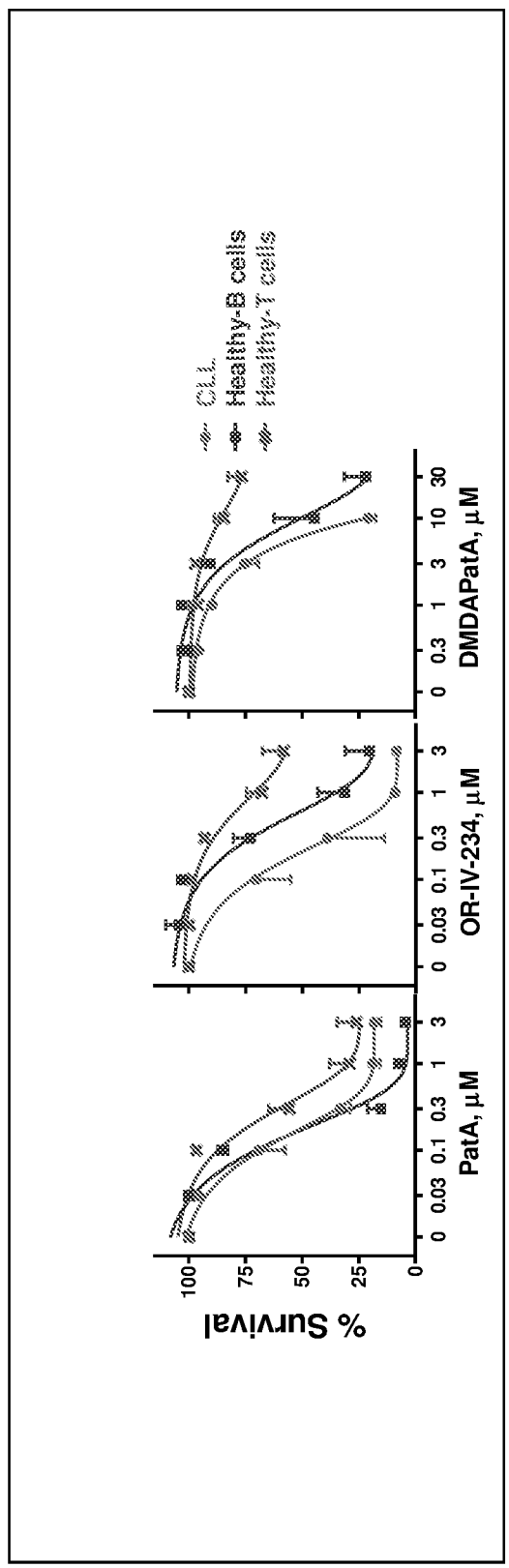
FIGS. 8A and 8B compare CLL cell potency to B and T cells from normal (healthy) donors for a representative pateamine A derivative (OR-IV-234) with PatA and DMDAPatA as controls. Percent survival as a function of derivative concentration is shown in FIG. 8A and $IC_{50}$ values are summarized in FIG. 8B.
Figure 8B:
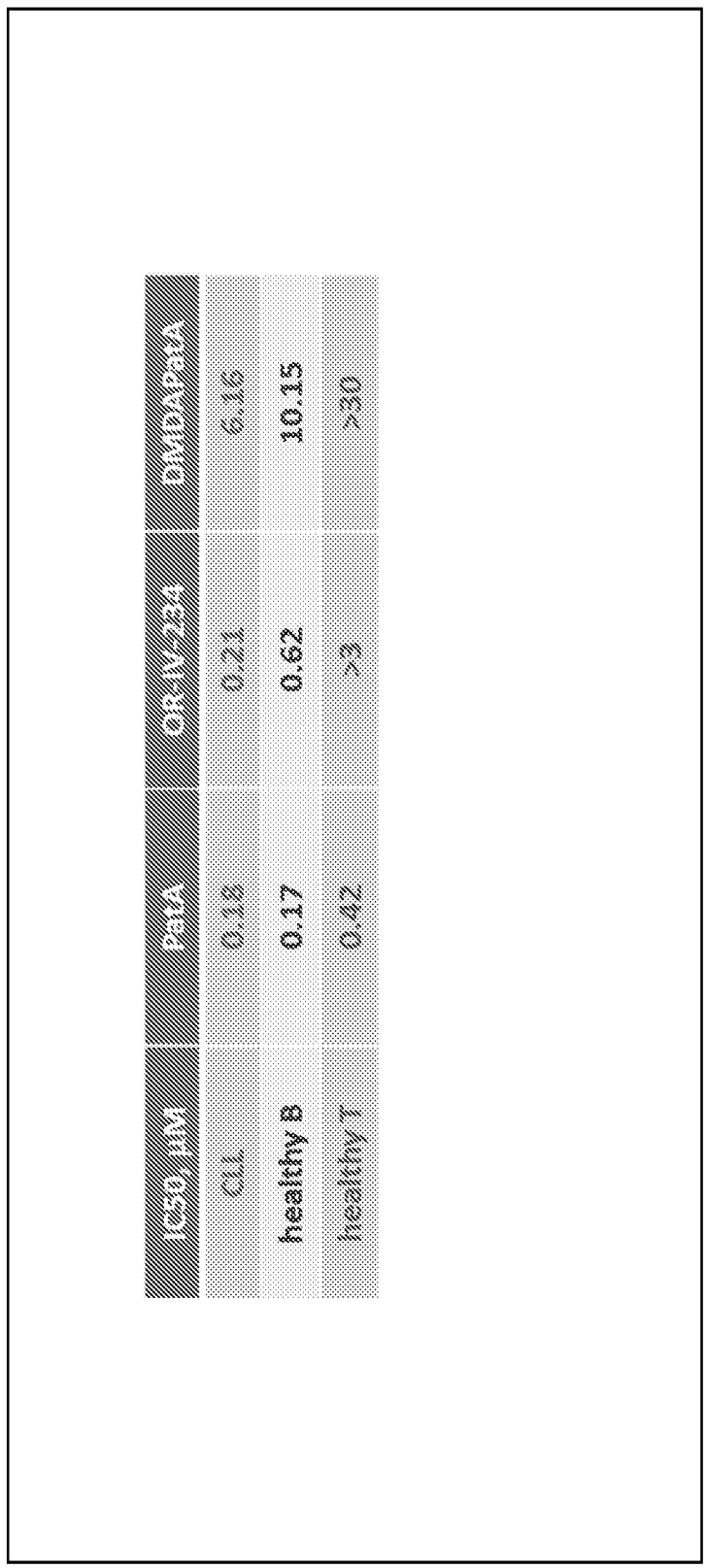

To predict the therapeutic window of the PatA analogs, their cellular toxicity was compared to CLL cells and to B and T cells from normal donors (FIGS. 8A and 8B). The data showed that PatA was similarly toxic to CLL cells as well as normal B and T cells. PatA was originally identified as a biological probe that inhibits T cell activation, consistent with its toxicity to T cells. It is interesting that all the PatA analogs demonstrated much less T cell toxicity, as well as less killing toward normal B cells, indicating a significant improvement of therapeutic window.

Figure 9A:
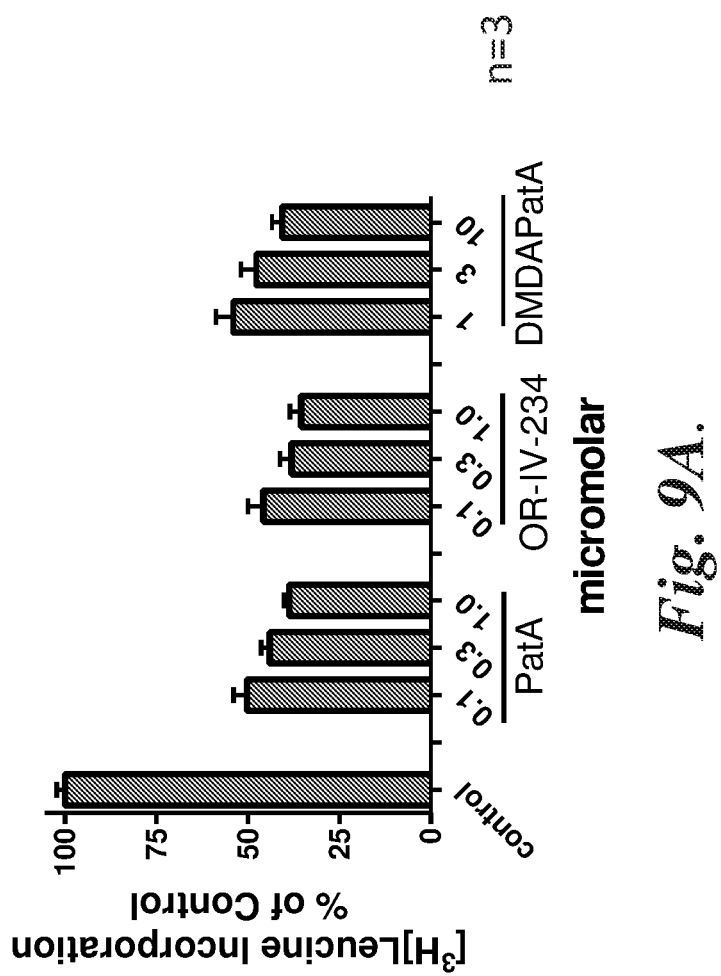
FIGS. 9A and 9B illustrate inhibition of protein synthesis (leucine incorporation analysis) for a representative pateamine A derivative (OR-IV-234) (FIG. 9A) and compared to DMDAPatA and PatA. All derivatives demonstrated strong inhibition of protein synthesis and the reduction of Mcl-1 level was confirmed by immunoblots (FIG. 9B). Apoptosis was demonstrated by the reduction of CLL cell survival shown below the blots.
Figure 9B:
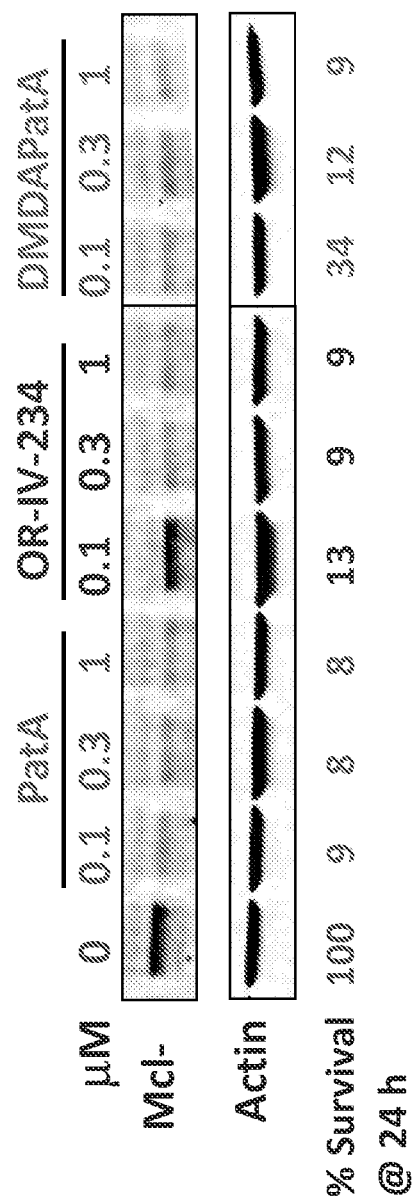

To confirm that the analogs retain the inhibition on protein synthesis, leucine incorporation analysis was performed on the analogs (FIG. 9A) and compared to DMDAPatA and PatA. In three CLL samples tested, all analogs demonstrated strong inhibition of protein synthesis and the reduction of Mcl-1 level was confirmed by immunoblots (FIG. 9B). Apoptosis was demonstrated by the reduction of CLL cell survival shown below the blots.

The PatA analog DMDAPatA induced apoptosis in primary CLL cells through the intrinsic pathway regardless of patient prognosis characters and reduced the short-lived anti-apoptotic protein Mcl-1, but not Bcl-2. DMDAPatA and ABT-199 target two parallel arms of apoptosis regulation and induce cell death synergistically, indicating that they could be used effectively in combination to treat CLL. As expected, DMDAPatA was >99% bound in human plasma. A series of PatA derivatives was synthesized and several of them exhibited greater cytotoxic potency toward CLL cells and lower human plasma protein binding. These studies demonstrate that inhibition of protein translation through perturbation of eIF4A by PatA analogs is a valid therapeutic strategy for CLL either alone or in mechanism-based combinations. Taken together, three new lead PatA analogs with potent inhibition of protein translation have been identified. These analogs retained toxicity toward primary CLL cells and exhibited improved selectivity over normal lymphocytes and reduced plasma protein binding. These compounds hold great promise for application of patient-specific disease with the right biological context, such as CLL, in which the leukemia cells are addicted to the sustained expression of Mcl-1 for survival.

The following examples are provided for the purpose of illustrating, not limiting the invention.

EXAMPLES

General Methods

All reactions were carried out under nitrogen atmosphere in flame-dried glassware. Acetonitrile, dichloromethane, methanol, and tetrahydrofuran were purified by passage through activated molecular sieves or alumina (solvent system). Dimethylformamide (DMF) was purchased and dried over 4 Å molecular sieves. All commercial reagents were used as received. ¹H NMR spectra were recorded on INOVA-500. ¹H NMR chemical shifts are reported as δ values in ppm relative to CDCl$_3$ (7.26 ppm), coupling constants (J) are reported in Hertz (Hz), and multiplicity follows convention. Flash column chromatography was performed using 60 Å Silica Gel as a stationary phase using a gradient solvent system (EtOAc/hexanes as eluent unless specified otherwise). Purification by prep-HPLC was performed on the Agilent 1260 Infinity Preparative-Scale Purification System using a Gemini HPLC column (C18, 5 micron, 100×21.20 mm). Mass spectra were obtained at the center for Chemical Characterization and Analysis (Texas A&M University). Thin layer chromatography (TLC) was performed using glass-backed silica gel 60F$_{254}$.

Example 1

The Preparation of Representative β-Amino Pateamine A Derivatives

In this example, the preparations of representative β-amino pateamine A derivatives of the invention, Compounds 13 (OR-IV-211), 14 (MZ732), and 15 (OR-IV-234), are described. The preparation is illustrated schematically in FIGS. 1 and 2.

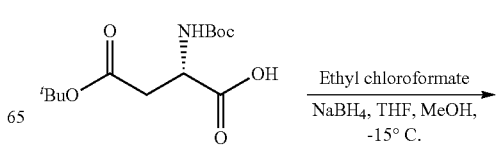

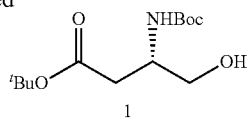

tert-Butyl (S)-3-((tert-butoxycarbonyl)amino)-4-hydroxybutanoate (1)

The aspartic acid derivative (5.0 g, 17.28 mmol) was dissolved in anhydrous THF (100 mL) and then the solution was cooled to −15° C. The triethylamine (2.41 mL, 17.28 mmol) was then added slowly dropwise, followed by the ethyl chloroformate (1.65 mL, 17.28 mmol). The reaction mixture was stirred at the same temperature for 15 minutes, and then the sodium borohydride (1.96 g, 51.84 mmol) was added, followed by the slow addition of methanol (100 mL) over a period of 30 minutes at −15° C. The solution was further stirred for 30 minutes and then neutralized with 0.5N HCl (to pH 7). The organic solvents were removed under reduced pressure and then the residue was diluted with water (100 mL), extracted with ethyl acetate (3×150 mL). The combined organic fractions were dried over sodium sulfate, filtered and concentrated under reduced pressure. The residue was dried under high vacuum and gave the desired product 1 as a colorless oil (4.76 g) and used for the next reaction without further purification. $^1$H NMR (500 MHz, CDCl$_3$) δ 5.47 (bs, 1H), 5.23 (bs, 1H), 3.99-3.93 (m, 1H), 3.68 (d, J=5.0 Hz, 2H), 2.57-2.47 (m, 2H), 1.45 (s, 9H), 1.43 (s, 9H). $^{13}$C NMR (150 MHz, CDCl$_3$) δ 171.2, 155.9, 81.1, 79.6, 64.3, 49.7, 37.5, 28.4 (3C), 28.0 (3C). HRMS (ESI$^+$): Calcd. for C$_{13}$H$_{25}$NNaO$_5$$^+$ ([M+Na]$^+$): 298.1625. Found: 298.1611.

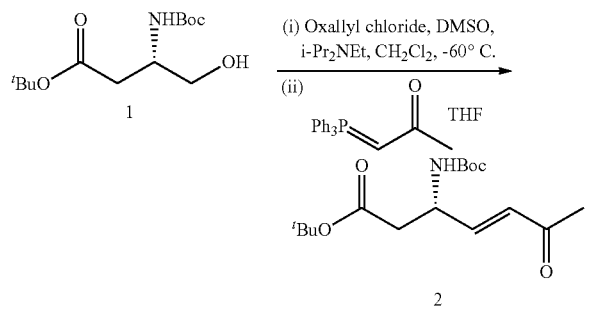

tert-Butyl (S,E)-3-((tert-butoxycarbonyl)amino)-6-oxohept-4-enoate (2)

The oxalyl chloride (2.49 mL, 28.51 mmol) was dissolved in anhydrous dichloromethane (50 mL) and then the solution was cooled to −60° C. A solution of anhydrous dimethyl sulfoxide (4.05 mL, 57.01 mmol, in 10 mL of dichloromethane) was then added slowly dropwise over 15 minutes. The aminoalcohol (4.76 g, 17.28 mmol) was then added slowly over a 10 minutes period. The resulting mixture was stirred for 15 minutes at −60° C. and then the diisopropylethylamine (18.06 mL, 103.66 mmol, in 50 mL of dichloromethane) was added dropwise over 15 minutes. The reaction mixture was stirred for 30 minutes at −60° C. and then quenched by the addition of 5 mL of water. The resulting slurry was poured into 300 mL of diethyl ether and washed with a 20% aqueous solution of KHSO$_4$ (2×100 mL). The organic fraction was dried over sodium sulfate, filtered and concentrated under reduced pressure to afford the crude aldehyde, which was used immediately for the next reaction without any further purification.

The crude aldehyde was dissolved in anhydrous THF (100 mL) and then the solution was cooled to 0° C. The triphenylphosphoranylidene was then added and the reaction mixture was allowed to warm up to 22° C. and stirred at this temperature for 12 hours. The mixture was then concentrated under reduced pressure and resuspended in diethyl ether (100 mL) and filtered through celite to remove the triphenylphosphine oxide side product, and the filtrate was then concentrated under reduced pressure. The residue was purified by MPLC on silica gel using a gradient of hexanes and ethyl acetate (9:1→1:9) and afforded the desired product 2 as a colorless oil (2.78 g, 51%, for three steps). $^1$H NMR (500 MHz, CDCl$_3$) δ 6.69 (dd, J=16.0, 5.0 Hz, 1H), 6.14 (d, J=16.0 Hz, 1H), 5.38 (bs, 1H), 4.70-4.55 (m, 1H), 2.58 (dd, J=15.5, 5.5 Hz, 1H), 2.51 (dd, J=15.5, 6.0 Hz, 1H), 2.22 (s, 3H), 1.41 (s, 9H), 1.40 (s, 9H). $^{13}$C NMR (150 MHz, CDCl$_3$) δ 198.1, 170.0, 155.0, 145.8, 130.2, 81.9, 80.0, 60.5, 48.4, 39.8, 28.4 (3C), 28.1 (3C). LRMS (APCI$^-$): Calcd. for C$_{16}$H$_{26}$NO$_5$$^-$ ([M−H]$^-$), 312.18. Found: 311.99.

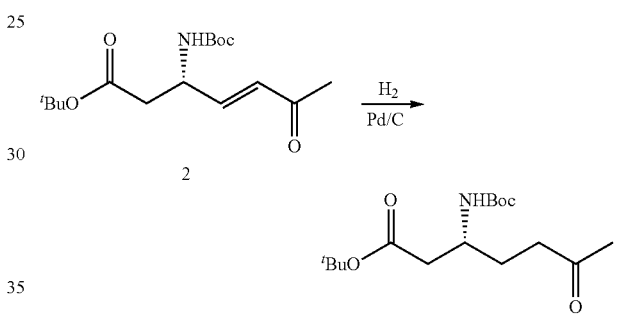

tert-Butyl (R)-3-((tert-butoxycarbonyl)amino)-6-oxoheptanoate (3)

The enone (2.5 g, 7.98 mmol) was dissolved in ethyl acetate (54 mL) and EtOH (6 mL). The palladium catalyst (0.25 g, Pd/C 10% w/w) was then added, and then the mixture was stirred under an atmosphere of hydrogen (balloon) at 22° C. for 15 hours. The mixture was purged with nitrogen and then filtered through a short celite pad. The filtrate was concentrated under reduced pressure and the residue was purified by MPLC on silica gel using a gradient of hexanes and ethyl acetate (8:2→1:9) and afforded the desired product 3 as a colorless oil (1.36 g, 54%). $^1$H NMR (500 MHz, CDCl$_3$) δ 4.99 (d, J=9.0 Hz, 1H), 3.92-3.80 (m, 1H), 2.56-2.49 (m, 2H), 2.43-2.35 (m, 2H), 2.14 (s, 3H), 1.87-1.77 (m, 1H), 1.75-1.66 (m, 1H), 1.44 (s, 9H), 1.42 (s, 9H). $^{13}$C NMR (150 MHz, CDCl$_3$) δ 208.3, 170.9, 155.6, 81.2, 79.3, 47.5, 41.1, 40.3, 30.2, 28.5 (3C), 28.2 (3C). LRMS (APCI$^+$): Calcd. for C$_{16}$H$_{29}$NNaO$_5$$^+$ ([M+Na]$^+$), 338.19. Found: 338.31.

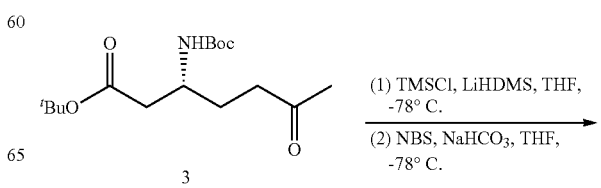

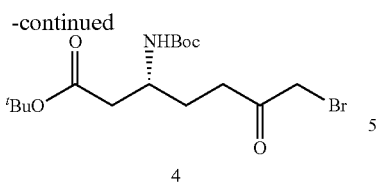

tert-Butyl (R)-7-bromo-3-((tert-butoxycarbonyl)amino)-6-oxoheptanoate (4)

n-Butyllithium (3.24 mL, 8.09 mmol, 2.5 M in hexanes) was slowly added to a solution of 1,1,1,3,3,3-hexamethyldisilazane (1.70 mL, 8.09 mmol) in THF (50 mL) at −78° C. The solution was stirred for 15 minutes at −78° C. and then for 20 minutes at 0° C. The mixture was cooled to −78° C. and then chlorotrimethylsilane (1.4 mL, 11.03 mmol) was slowly added followed by the methyl ketone 3 (1.16 g, 3.68 mmol, in 20 mL of THF). After 20 minutes anhydrous triethylamine (8 mL) was slowly added. The mixture was continued to stir for 5 minutes, and then quenched with 50 mL of a saturated aqueous NaHCO₃ solution, and extracted with ethyl acetate (3×50 mL). The combined organic fractions were dried over sodium sulfate, filtered and concentrated under reduced pressure. The residue was dissolved in 10 mL of THF and the solution was added to a stirred suspension of N-bromosuccinimide (0.655 g, 3.68 mmol) and NaHCO₃ (0.340 g, 4.05 mmol) in THF (60 mL) at −78° C. After stirring for 1.5 hours at −78° C., the reaction was quenched by adding 30 mL of a saturated aqueous NaHCO₃ solution, and the mixture was extracted with ethyl acetate (3×50 mL). The combined organic fractions were dried over sodium sulfate, filtered and concentrated under reduced pressure. The crude residue was purified by MPLC on silica gel using a gradient of hexanes and ethyl acetate (9:1→1:1) and afforded the desired product 4 as a light yellow oil (0.668 g, 46%, for two steps). $^{1}$H NMR (500 MHz, CDCl$_3$) δ 5.04 (d, J=9.5 Hz, 1H), 3.93 (d, J=13.0 Hz, 1H), 3.90 (d, J=13.0 Hz, 1H), 3.89-3.82 (m, 1H), 2.78-2.66 (m, 2H), 2.46 (dd, J=15.5, 5.5 Hz, 1H), 2.38 (dd, J=15.5, 6.0 Hz, 1H), 1.90-1.83 (m, 1H), 1.77-1.70 (m, 1H), 1.44 (s, 9H), 1.42 (s, 9H). LRMS (ESI$^+$): Calcd. for C$_{16}$H$_{28}$BrNNaO$_5^+$ ([M+Na]$^+$): 416.1043. Found: 416.1024.

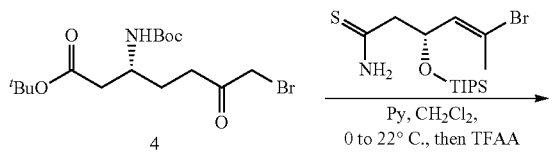

tert-Butyl (R)-5-(2-((R,E)-4-bromo-2-((triisopropylsilyl)oxy)pent-3-en-1-yl)thiazol-4-yl)-3-((tert-butoxycarbonyl)amino)pentanoate (5)

The α-bromoketo ester 4 (0.636 g, 1.61 mmol) was dissolved in dichloromethane (16 mL) and then the solution was cooled to 0° C. The thioamide (0.614 g, 1.61 mmol) was added, followed by the pyridine (0.325 mL, 4.03 mmol). The reaction mixture was allowed to warm up to 22° C. and then stirred for 18 hours at 22° C. The mixture was cooled to 0° C. and then the trifluoroacetic anhydride (0.273 mL, 1.94 mmol) was added. The reaction mixture was allowed to warm up to 22° C. and then stirred for 3 hours at 22° C., then quenched with 15 mL of a saturated aqueous NaHCO₃ solution, and extracted with dichloromethane (3×50 mL). The combined organic fractions were dried over sodium sulfate, filtered and concentrated under reduced pressure. The crude residue was purified by MPLC on silica gel using a gradient of hexanes and ethyl acetate (9:1→1:1) and afforded the desired product 5 as a light yellow oil (0.540 g, 50%). $^{1}$H NMR (500 MHz, CDCl$_3$) δ 6.83 (s, 1H), 5.87 (dd, J=9.0, 1.5 Hz, 1H), 5.09 (d, J=9.0 Hz, 1H), 4.77 (dt, J=9.0, 6.5 Hz, 1H), 4.00-3.92 (m, 1H), 3.23 (dd, J=14.0, 6.0 Hz, 1H), 3.09 (dd, J=14.0, 6.5 Hz, 1H), 2.85-2.72 (m, 2H), 2.47 (dd, J=15.0, 5.0 Hz, 1H), 2.41 (dd, J=15.0, 6.0 Hz, 1H), 2.08 (s, 3H), 1.92-1.82 (m, 2H), 1.44 (s, 9H), 1.43 (s, 9H), 1.04-1.00 (m, 21H). $^{13}$C NMR (150 MHz, CDCl$_3$) δ 170.9, 165.2, 156.0, 155.4, 134.9, 121.3, 113.6, 80.8, 78.9, 70.2, 47.5, 41.9, 40.7, 34.4, 28.4 (3C), 28.1, 28.0 (3C), 23.9, 18.0 (3C), 17.8 (3C), 12.3 (3C). LRMS (APCI$^+$): Calcd. for C$_{31}$H$_{56}$BrN$_2$O$_5$SSi$^+$ ([M+H]$^+$), 675.28. Found: 675.22.

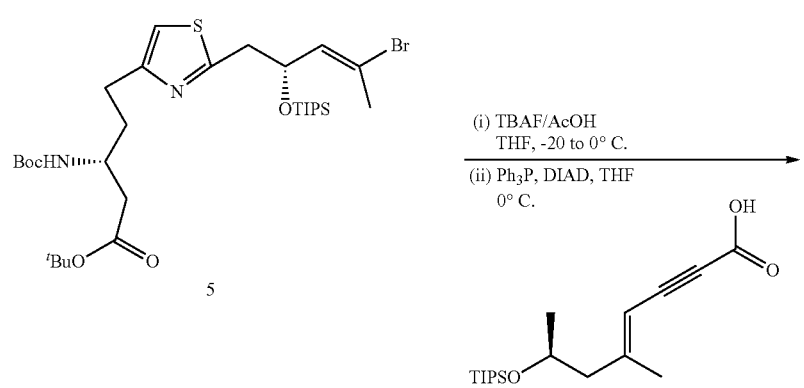

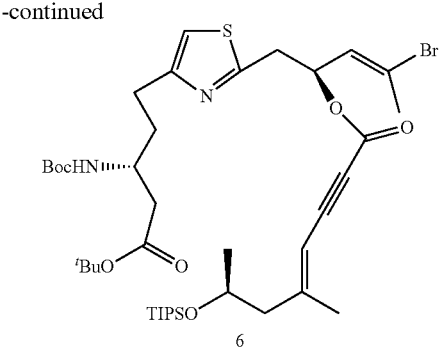

6

(S,E)-4-Bromo-1-(4-((R)-5-(tert-butoxy)-3-((tert-butoxycarbonyl)amino)-5-oxopentyl) thiazol-2-yl) pent-3-en-2-yl (S,E)-5-methyl-7-((triisopropylsilyl) oxy)oct-4-en-2-ynoate (6)

The thiazole ester 5 (0.510 g, 0.755 mmol) was dissolved in THF (10 mL) and then the solution was cooled to −20° C. A pre-mixed solution of tetrabutylammonium fluoride (1.13 mL, 1.13 mmol, 1M in THF) and acetic acid (13 μL, 0.226 mmol) was added dropwise and then the reaction mixture was stirred at 0° C. for 6 hours. The mixture was diluted with dichloromethane (20 mL) and washed with 15 mL of a saturated aqueous $NaHCO_3$ solution. The organic fraction was dried over sodium sulfate, filtered and concentrated under reduced pressure. The residue was dissolved in THF (10 mL) and then enyne acid (0.318 g, 0.981 mmol) was added, followed by the triphenylphosphine (0.495 g, 1.89 mmol). The mixture was cooled to 0° C. and then the DIAD (0.444 mL, 2.26 mmol) was added dropwise. The reaction mixture was allowed to warm up to 22° C. and then the reaction mixture was stirred at 22° C. for 8 hours. The reaction was quenched with 15 mL of a pH 7 buffer solution and extracted with dichloromethane (3×50 mL). The combined organic fractions were dried over sodium sulfate, filtered and concentrated under reduced pressure. The crude residue was purified by MPLC on silica gel using a gradient of hexanes and ethyl acetate (9:1→1:1) and afforded the desired product 6 as a light yellow oil (0.437 g, 70%). $^1$H NMR (500 MHz, $CDCl_3$) δ 6.88 (s, 1H), 5.87 (d, J=9.5 Hz, 1H), 5.77 (dt, J=9.5, 6.7 Hz, 1H), 5.40 (s, 1H), 5.05 (d, J=9.7 Hz, 1H), 4.14-4.09 (m, 1H), 3.98-3.92 (m, 1H), 3.38 (dd, J=14.7, 6.9 Hz, 1H), 3.25 (dd, J=14.7, 6.6 Hz, 1H), 2.85-2.73 (m, 2H), 2.48-2.41 (m, 2H), 2.41 (dd, J=13.2, 6.0 Hz, 1H), 2.27 (s, 3H), 2.25 (dd, J=13.2, 7.0 Hz, 1H), 2.01 (s, 3H), 1.91-1.86 (m, 2H), 1.43 (s, 18H), 1.15 (d, J=6.2 Hz, 3H), 1.05 (s, 21H). $^{13}$C NMR (150 MHz, $CDCl_3$) δ 171.1, 164.0, 159.3, 156.1, 155.6, 153.2, 128.5, 128.1, 114.5, 105.0, 86.2, 83.5, 81.2, 79.3, 71.4, 67.2, 49.7, 47.5, 40.9, 37.7, 34.4, 28.6 (3C), 28.2 (3C), 28.1, 24.5, 23.6, 21.2, 18.28 (3C), 18.26 (3C), 12.6 (3C). LRMS ($APCI^+$): Calcd. for $C_{40}H_{66}BrN_2O_7SSi$ ($[M+H]^+$), 825.34. Found: 825.34.

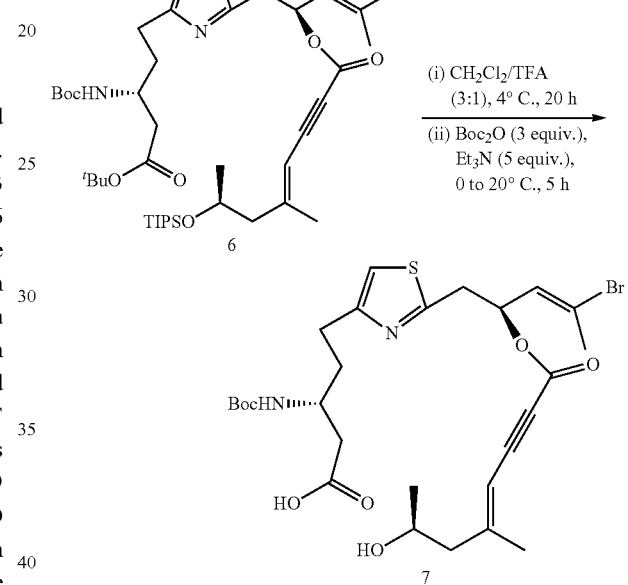

(R)-5-(2-(((S,E)-4-bromo-2-(((S,E)-7-hydroxy-5-methyloct-4-en-2-ynoyl)oxy)pent-3-en-1-yl)-3l4-thiazol-4-yl)-3-((tert-butoxycarbonyl)amino)pentanoic Acid (7)

To a solution of 6 (108 mg, 0.131 mmol, 1.0 equiv) in 2.5 mL of DCM was slowly added 1.0 mL of TFA at 0° C. under $N_2$. The solution was kept at 4° C. for 20 hours, diluted with 10 mL of toluene and concentrated in vacuo. The residue was dissolved in 5 mL of dioxane and 0.5 mL of $H_2O$, cooled to 0° C., then $Boc_2O$ (85 μL, 0.392 mmol, 3 equiv) and $Et_3N$ (92 mL, 0.655 mmol, 5 equiv) were added. The solution was stirred at 20° C. for 15 h, diluted with 100 mL of EtOAc, transferred to a separation funnel, acidified by adding 1 mL of aq. HCl (1M), and washed with brine (5 mL). The organic layer was dried over $MgSO_4$ and concentrated in vacuo. The residue was purified by flash chromatography (hexanes: acetone=5:1→5:2) to give the desired product 7 as a colorless oil (41 mg, 51%). $R_f$=0.41 (hexanes:acetone=5:3) $^1$H NMR (500 MHz, $CDCl_3$, COOH and OH not observed) δ 6.90 (s, 1H), 5.88 (d, J=9.0 Hz, 1H), 5.82-5.76 (m, 1H), 5.46 (s, 1H), 5.32-5.29 (m, 1H), 4.05-4.00 (m, 1H), 3.97-3.90 (m, 1H), 3.39 (dd, J=14.7, 7.4 Hz, 1H), 3.30 (dd, J=14.7, 5.5 Hz, 1H), 2.88-2.74 (m, 2H), 2.58 (brs, 2H), 2.31-2.25 (m, 2H), 2.30 (s, 3H), 2.01 (s, 3H), 1.97-1.90 (m, 2H), 1.44 (s, 9H), 1.22 (d, J 6.2 Hz, 3H). $^{13}$C NMR (150 MHz, CDCl$_3$) δ 174.8, 164.5, 158.5, 156.2, 155.9, 153.2, 128.5, 128.1, 114.5, 105.1, 85.8, 83.6, 79.7, 71.5, 65.9, 48.8, 47.4, 39.5, 37.6, 34.2, 29.9, 28.6 (3C), 24.5, 23.6, 20.7. LRMS (ESI$^-$): Calcd. for C$_{27}$H$_{37}$BrN$_2$O$_7$S ([M–H]$^-$), 611.1. Found: 611.1.

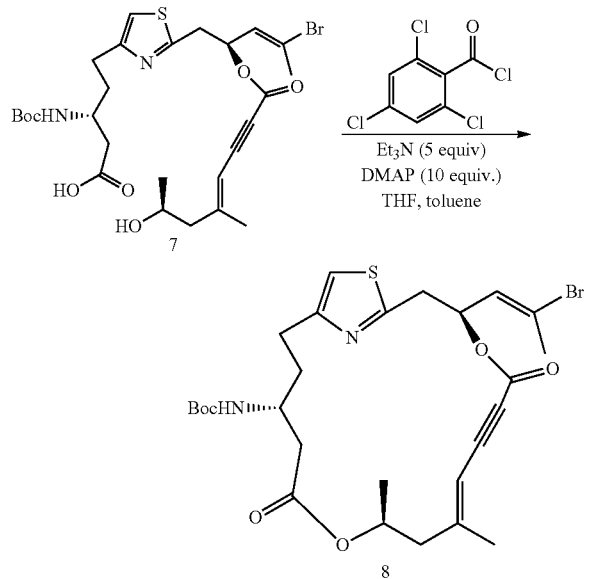

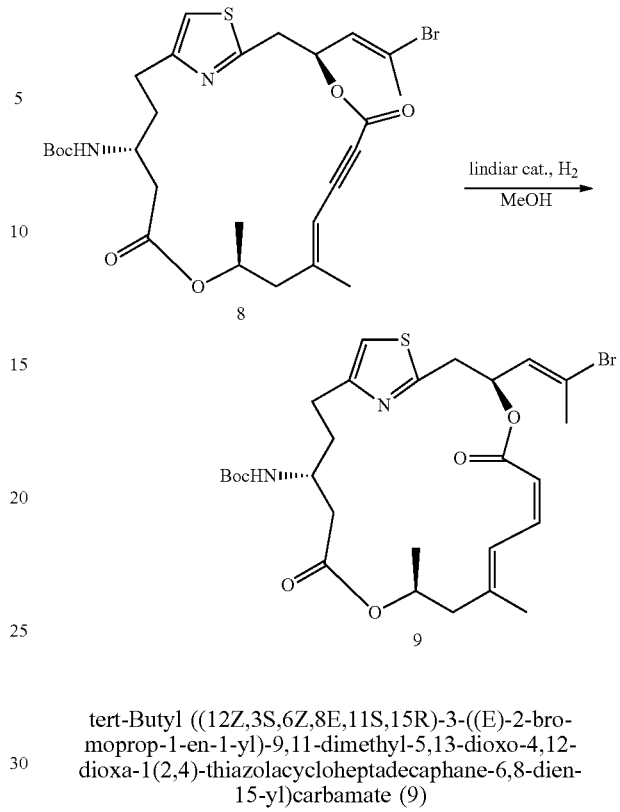

tert-Butyl ((12Z,3S,8E,11S,15R)-3-((E)-2-bromoprop-1-en-1-yl)-9,11-dimethyl-5,13-dioxo-4,12-dioxa-1(2,4)-thiazolacycloheptadecaphane-6-yn-8-en-15-yl)carbamate (8)

To a solution of 7 (38 mg, 0.0169 mmol, 1 equiv) in 6 mL of THF were added 2,4,6-trichlorobenzoyl chloride (48 μL, 0.310 mmol, 5 equiv) followed by Et$_3$N (43 μL, 0.310 mmol, 5 equiv). After stirring for 30 min, the solution was transferred to a solution of DMAP (76 mg, 0.619 mmol, 10 equiv) in 150 mL of toluene and the stirring was kept for 48 hours at 20° C. The mixture was washed with brine, dried over MgSO$_4$ and concentrated. The residue was purified by flash chromatography (hexanes:ethyl acetate=5:1) to give the desired product 8 as a colorless oil (27 mg, 73%). R$_f$=0.55 (hexanes:ethyl acetate=2:1). $^1$H NMR (500 MHz, CDCl$_3$) δ 6.83 (s, 1H), 6.04-6.01 (m, 1H), 5.85 (td, J=8.8, 3.8 Hz, 1H), 5.34 (s, 1H), 5.31-5.26 (m, 1H), 4.55 (d, J=9.0 Hz, 1H), 3.97-3.91 (m, 1H), 3.33 (dd, J=15.3, 3.9 Hz, 1H), 3.37 (dd, J=15.3, 8.4 Hz, 1H), 2.85-2.79 (m, 1H), 2.75-2.69 (m, 2H), 2.39 (d, J=1.3 Hz, 3H), 2.31-2.26 (m, 3H), 2.00-1.95 (m, 2H), 1.92 (s, 3H), 1.44 (s, 9H), 1.25 (d, J=6.5 Hz, 3H). $^{13}$C NMR (150 MHz, CDCl$_3$) δ 170.3, 163.6, 158.3, 156.7, 155.5, 153.4, 128.9, 127.3, 144.0, 105.8, 85.1, 84.0, 79.7, 70.8, 67.1, 47.8, 46.7, 40.2, 37.8, 34.7, 29.1, 28.6 (3C), 34.6, 21.0, 20.2. HRMS (ESI$^+$): Calcd. for C$_{27}$H$_{36}$BrN$_2$O$_6$S ([M+H]$^+$), 595.1477. Found: 595.1451.

tert-Butyl ((12Z,3S,6Z,8E,11S,15R)-3-((E)-2-bromoprop-1-en-1-yl)-9,11-dimethyl-5,13-dioxo-4,12-dioxa-1(2,4)-thiazolacycloheptadecaphane-6,8-dien-15-yl)carbamate (9)

A round-bottomed flask was charged with eneyne 8 (25 mg, 0.042 mmol), lindlar catalyst (17.5 mg, 70% w/w) and methanol (2 mL). A hydrogen balloon was put on the top of the flask and the mixture was stirred at 20° C. for 4 hours until no starting material visible on TLC. The mixture was filtered through a cotton pad which was rinsed with 5 mL of EtOAc. The solvents were evaporated in vacuo and the crude residue was purified on a silica gel chromatography (CH$_2$Cl$_2$:Et$_2$O=8:1) to provide the product 9 as a colorless oil (18 mg, 72%). R$_f$=0.45 (hexanes:ethyl acetate=3:1). $^1$H NMR (500 MHz, CDCl$_3$) δ 6.98 (d, J=11.8 Hz, 1H), 6.79 (s, 1H), 6.70 (t, J=11.8 Hz, 1H), 6.05 (td, J=9.4, 4.7 Hz, 1H), 5.96 (dq, J=9.5, 1.3 Hz, 1H), 5.34 (d, J=11.8 Hz, 1H), 5.14-5.08 (m, 1H), 4.67 (brs, 1H), 3.62 (brs, 1H), 3.21-3.14 (m, 2H), 2.81 (dt, J=14.5, 6.1 Hz, 1H), 2.70 (dt, J=14.5, 7.7 Hz, 1H), 2.48 (s, 3H), 2.41-2.30 (m, 3H), 2.15 (d, J=13.4 Hz, 1H), 1.98-1.88 (m, 2H), 1.84 (s, 3H), 1.42 (s, 9H), 1.25 (d, J=6.3 Hz, 3H). $^{13}$C NMR (150 MHz, CDCl$_3$) δ 170.6, 164.9, 164.7, 156.7, 155.5, 146.4, 141.4, 129.9, 127.0, 123.9, 114.9, 113.7, 79.3, 69.0, 68.0, 48.1, 47.5, 40.1, 38.4, 36.8, 33.9, 28.6 (3C), 24.7, 21.4, 17.1. HRMS (ESI$^+$): Calcd. for C$_{27}$H$_{38}$BrN$_2$O$_6$S ([M+H]$^+$), 597.1634. Found: 597.1667.

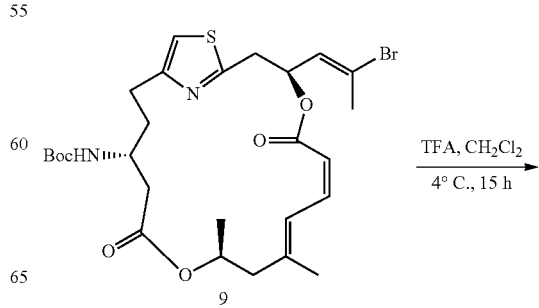

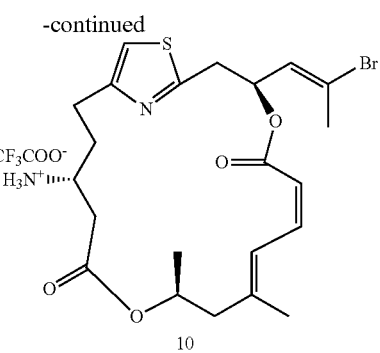

(12Z,3S,6Z,8E,11S,15R)-15-amino-3-((E)-2-bromoprop-1-en-1-yl)-9,11-dimethyl-4,12-dioxa-1(2,4)-thiazolacycloheptadecaphane-6,8-diene-5,13-dione (10)

A solution of trifluoroacetic acid (0.3 mL) in DCM (1.2 mL) was cooled to 0° C. and added to carbamate 9 (8.0 mg, 0.013 mmol) at 0° C. under $N_2$. The reaction was kept in a 4° C. refrigerator for 15 hours, then 10 mL of $CHCl_3$ was added and the solvents were evaporated while the flask was kept at 0° C. The crude residue was purified by a silica gel chromatography (dichloromethane:MeOH=20:1) to give the product 10 as a colorless oil in the form of a TFA salt (9 mg, 99%). $^1H$ NMR (500 MHz, $CDCl_3$) δ 7.96 (brs, 3H), 7.19 (s, 1H), 6.80 (d, J=11.7 Hz, 1H), 6.71 (t, J=11.7 Hz, 1H), 6.12 (t, J=11.4 Hz, 1H), 5.94 (d, J=9.3 Hz, 1H), 5.36 (d, J=11.4 Hz, 1H), 5.20-5.17 (m, 1H), 3.26-3.31 (m, 1H), 3.22-3.14 (m, 2H), 3.03-2.95 (m, 2H), 2.85-2.80 (m, 1H), 2.64-2.60 (m, 1H), 2.45 (s, 3H), 2.35-2.31 (m, 1H), 2.22-2.15 (m, 1H), 2.15 (d, J=12.8 Hz, 1H), 2.08-2.00 (m, 1H), 1.84 (s, 3H), 1.28 (d, J=6.4 Hz, 3H). HRMS ($ESI^+$): Calcd. for $C_{22}H_{30}BrN_2O_4S$ ($[M+H]^+$), 497.1104. Found: 497.1099.

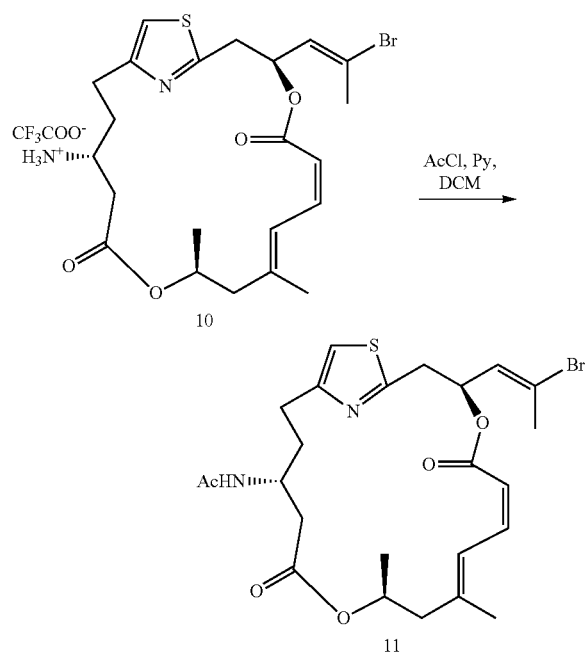

N-((12Z,3S,6Z,8E,11S,15R)-3-((E)-2-bromoprop-1-en-1-yl)-9,11-dimethyl-5,13-dioxo-4,12-dioxa-1(2,4)-thiazolacycloheptadecaphane-6,8-dien-15-yl)acetamide (11)

To a solution of amine 10 (10.0 mg, 0.0164 mmol, 1 equiv.) in 0.5 mL of $CH_2Cl_2$ were added pyridine (0.25 mL, excess) and AcCl (5.9 μL, 0.0828 mmol, 5 equiv.) at 0° C. The reaction flask was kept in a 4° C. fridge for 15 hours. The mixture was diluted with 25 mL of EtOAc, washed with $H_2O$ and brine. The organic phase was dried over $MgSO_4$ and concentrated in vacuo. The residue was purified by a flash chromatography (hexanes:acetone=2:1) to give the desired product 11 as a colorless oil (6.5 mg, 74%). $R_f$=0.41 (hexanes:acetone=2:1). $^1H$ NMR (500 MHz, $CDCl_3$) δ 7.01 (d, J=11.4 Hz, 1H), 6.81 (s, 1H), 6.74 (t, J=11.7 Hz, 1H), 6.06 (td, J=9.3, 5.5 Hz, 1H), 5.97 (dt, J=9.3, 1.1 Hz, 1H), 5.77 (d, J=7.9 Hz, 1H), 5.39 (d, J=11.4 Hz, 1H), 5.13-5.07 (m, 1H), 3.96 (sextet, J=7.0 Hz, 1H), 3.19-3.18 (m, 2H), 2.79-2.68 (m, 2H), 2.51 (dd, J=15.7, 7.4 Hz, 1H), 2.45 (s, 3H), 2.41 (dd, J=15.7, 5.7 Hz, 1H), 2.36 (dd, J=13.4, 10.8 Hz, 1H), 2.16 (d, J=13.4 Hz, 1H), 1.93 (s, 3H), 1.89-1.83 (m, 2H), 1.85 (s, 3H), 1.25 (d, J 6.4 Hz, 3H). HRMS ($ESI^+$): Calcd. for $C_{24}H_{32}BrN_2O_5S$ ($[M+H]^+$), 539.1210. Found: 539.1198.

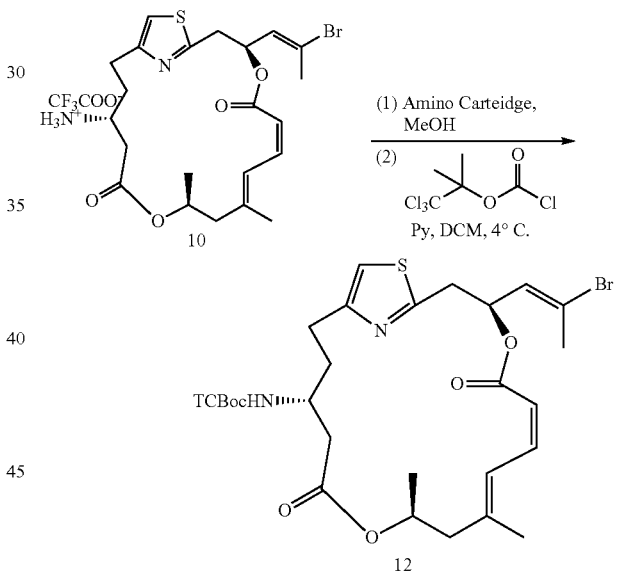

1,1,1-Trichloro-2-methylpropan-2-yl ((12Z,3S,6Z,8E,11S,15R)-3-((E)-2-bromoprop-1-en-1-yl)-9,11-dimethyl-5,13-dioxo-4,12-dioxa-1(2,4)-thiazolacycloheptadecaphane-6,8-dien-15-yl)carbamate (12)

Following the published procedure, (Romo, D., Rzasa, R. M., Shea, H. A., Park, K., Langenhan, J. M., Sun, L., Akhiezer, A., and Liu, J. O. (1998) Total Synthesis and Immunosuppressive Activity of (−)-Pateamine A and Related Compounds: Implementation of a β-Lactam-Based Macrocyclization, J. Am. Chem. Soc. 120, 12237-12254) compound 10 (4.3 mg, 0.0074 mmol) afforded the desired product 12 as a colorless oil (5.3 mg, 71%). $R_f$=0.28 (hexanes:ethyl acetate=4:1). $^1H$ NMR (500 MHz, $CDCl_3$) δ 7.00 (d, J=11.8 Hz, 1H), 6.79 (s, 1H), 6.72 (t, J=11.8 Hz, 1H), 6.06 (td, J=9.0, 5.3 Hz, 1H), 5.96 (d, J=9.4 Hz, 1H), 5.35 (d, J=11.6 Hz, 1H), 5.15-5.09 (m, 2H), 3.68-3.64 (m, 1H), 3.20-3.18 (m, 2H), 2.85-2.79 (m, 1H), 2.74-2.68 (m, 1H), 2.57 (dd, J=16.3, 8.3 Hz, 1H), 2.46 (s, 3H), 2.41-2.34 (m, 2H), 2.15 (d, J=13.0 Hz, 1H), 1.90 (s, 6H), 1.89-1.83 (m, 2H), 1.84 (s, 3H), 1.25 (d, J=6.3 Hz, 3H). $^{13}$C NMR (150 MHz, CDCl$_3$) δ 170.4, 165.7, 164.7, 160.9, 156.0, 153.8, 146.6, 141.7, 129.6, 127.4, 124.0, 114.7, 114.1, 106.8, 88.1, 68.9, 68.1, 48.0, 47.9, 40.0, 38.1, 33.5, 28.5, 24.8, 21.9 (2C). HRMS (ESI$^+$): Calcd. for $C_{27}H_{35}BrCl_3N_2O_6S$ ([M+H]$^+$), 699.0465. Found: 699.0437.

hours and transferred directly to a silica gel chromatography for purification (dichloromethane:MeOH:triethylamine=20:1:0.1). The product was further purified by the Prep-HPLC (solvent A: H$_2$O buffered with 8 mM HCOOH and 12 mM NH$_3$.H$_2$O, pH=9.0; solvent B: CH$_3$CN/H$_2$O (9:1 v/v) buffered with 8 mM HCOOH and 12 mM NH$_3$.H$_2$O; isocratic elution, solvent A/solvent B=1:4). The collected fractions were concentrated to give a mixture of the product and solid ammonium formate, upon which DCM (10 mL) was added and the suspension was filtered through a sintered Buchner

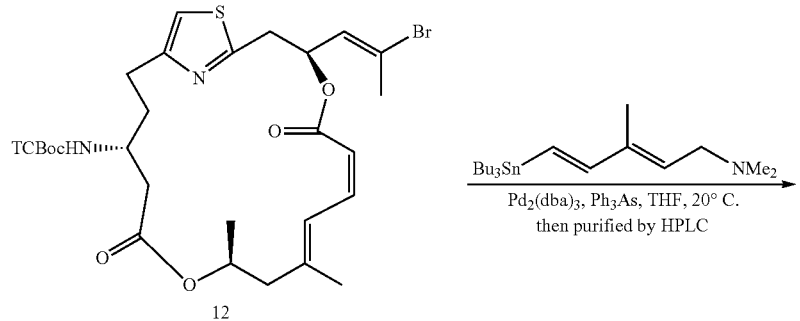

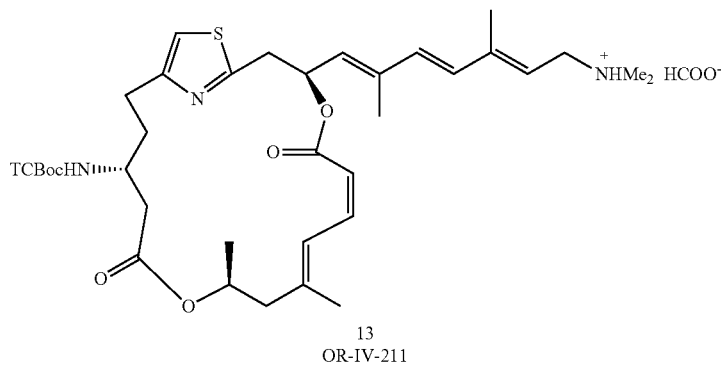

1,1,1-Trichloro-2-methylpropan-2-yl ((12Z,3S,6Z,8E,11S,15R)-3-((1E,3E,5E)-7-(dimethyl amino)-2-methylhepta-1,3,5-trien-1-yl)-9,11-dimethyl-5,13-dioxo-4,12-dioxa-1(2,4)-thiazolacycloheptadecaphane-6,8-dien-15-yl)carbamate (13 or OR-IV-211)

The coupling between 12 (4.5 mg, 0.0064 mmol, 1 equiv) and (2E,4E)-N,N,3-trimethyl-5-(tributylstannyl)penta-2,4-dien-1-amine (5.3 mg, 0.0128 mmol, 2 equiv) followed the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4A as potential anticancer agents, Bioorg. Med. Chem. 22, 116-125. The reaction mixture was kept at 20° C. for 15 glass funnel. The precipitates were rinsed with extra dichloromethane (2×5 mL). After concentration in vacuo the product 13 (OR-IV-211) was obtained as a colorless oil in the form a salt with formic acid (2.8 mg, 56%). $^1$H NMR (500 MHz, CDCl$_3$) δ 8.52 (s, 1H), 7.02 (d, J=11.9 Hz, 1H), 6.80 (s, 1H), 6.71 (t, J=11.7 Hz, 1H), 6.38 (d, J=15.9 Hz, 1H), 6.29 (d, J=15.9 Hz, 1H), 6.28-6.25 (m, 1H), 5.67 (t, J=7.5 Hz, 1H), 5.59 (d, J=9.0 Hz, 1H), 5.39 (d, J=11.4 Hz, 1H), 5.16-5.11 (m, 1H), 5.08 (d, J=8.1 Hz, 1H), 3.69-3.63 (m, 1H), 3.43 (d, J=7.5 Hz, 2H), 3.21-3.19 (m, 2H), 2.83 (dt, J=15.0, 6.3 Hz, 1H), 2.77-2.70 (m, 1H), 2.59 (dd. J=15.7, 8.3 Hz, 1H), 2.49 (s, 6H), 2.42-2.34 (m, 2H), 2.16 (d, J=13.3 Hz, 1H), 2.07-2.02 (m, 1H), 1.99 (d, J=1.0 Hz, 3H), 1.93-1.89 (m, 1H), 1.91 (s, 6H), 1.84 (s, 3H), 1.83 (s, 3H), 1.25 (d, J=6.1 Hz, 3H). HRMS (ESI$^+$): Calcd. for $C_{35}H_{49}Cl_3N_3O_6S$ ([M+H]$^+$), 744.2408. Found: 744.2429.

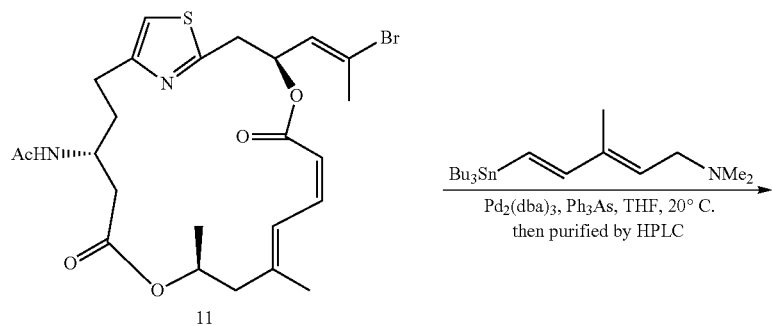

N-((12Z,3S,6Z,8E,11S,15R)-3-((1E,3E,5E)-7-(dimethylamino)-2,5-dimethylhepta-1,3,5-trien-1-yl)-9,11-dimethyl-5,13-dioxo-4,12-dioxa-1(2,4)-thiazolacycloheptadecaphane-6,8-dien-15-yl)acetamide (14 or MZ732)

The coupling between 11 (3.4 mg, 0.0063 mmol, 1 equiv) and (2E,4E)-N,N,3-trimethyl-5-(tributylstannyl)penta-2,4-dien-1-amine (5.2 mg, 0.0126 mmol, 2 equiv) was based on the known procedure. Low, W. K., Li, J., Zhu, M., Kommaraju, S. S., Shah-Mittal, J., Hull, K., Liu, J. O., and Romo, D. (2014) Second-generation derivatives of the eukaryotic translation initiation inhibitor pateamine A targeting eIF4A as potential anticancer agents, Bioorg. Med. Chem. 22, 116-125. The purification procedure was the same as that of 13 (OR-IV-211) to give the pure product 14 (MZ732) in the form of salt with formic acid as a colorless oil (1.8 mg, 49%). $^1$H NMR (500 MHz, CDCl$_3$) δ 8.23 (s, 1H), 7.03 (d, J 11.9 Hz, 1H), 6.82 (s, 1H), 6.74 (t, J=11.3 Hz, 1H), 6.39 (d, J=15.9 Hz, 1H), 6.34 (d, J 15.9 Hz, 1H), 6.29-6.25 (m, 1H), 5.84 (d, J=8.8 Hz, 1H), 5.69 (t, J=7.6 Hz, 1H), 5.63 (d, J=9.7 Hz, 1H), 5.43 (d, J=11.3 Hz, 1H), 5.13-5.09 (m, 1H), 4.01-3.98 (m, 1H), 3.68 (d, J=7.6 Hz, 2H), 3.21-3.19 (m, 2H), 2.79-2.74 (m, 2H), 2.67 (s, 6H), 2.50-2.46 (m, 2H), 2.35-2.32 (m, 1H), 2.16 (d, J=13.6 Hz, 1H), 1.99 (d, J=1.0 Hz, 3H), 1.97-1.93 (m, 2H), 1.95 (s, 3H), 1.87 (s, 3H), 1.86 (s, 3H), 1.25 (d, J=6.4 Hz, 3H). HRMS (ESI$^+$): Calcd. for C$_{32}$H$_{46}$N$_3$O$_5$S ([M+H]$^+$), 584.3158. Found: 584.3139.

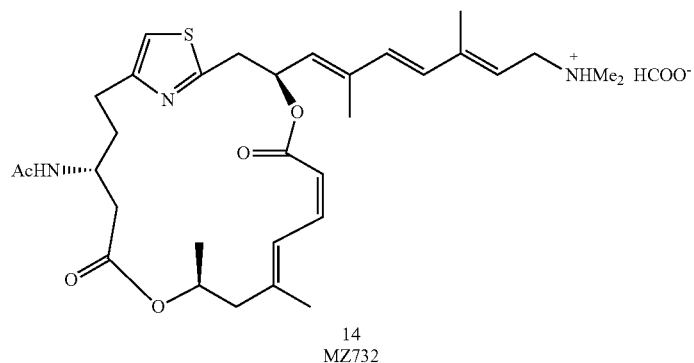

14
MZ732

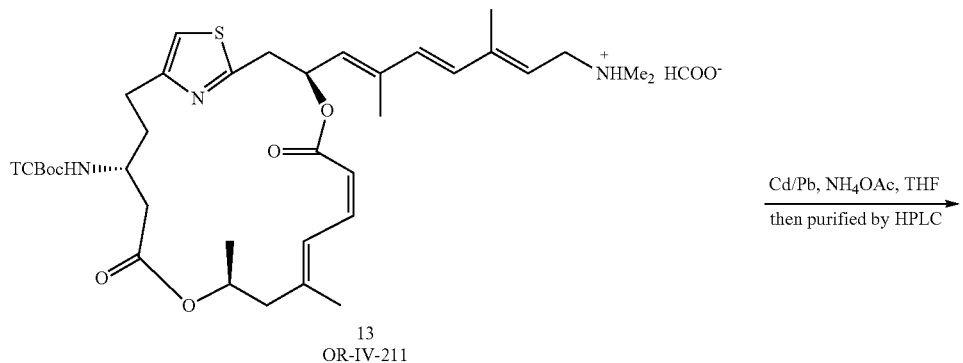

13
OR-IV-211

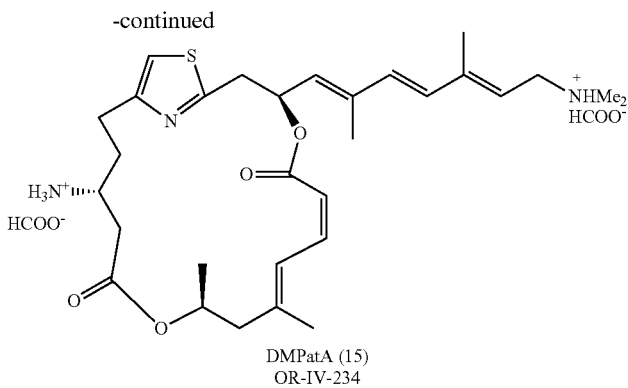

DMPatA (15)
OR-IV-234

(12Z,3S,6Z,8E,11S,15R)-15-amino-3-((1E,3E,5E)-7-(dimethylamino)-2,5-dimethylhepta-1,3,5-trien-1-yl)-9,11-dimethyl-4,12-dioxa-1(2,4)-thiazolacyclo-heptadecaphane-6,8-diene-5,13-dione, Des-Methyl-Pateamine A (DMPatA) (15 or OR-IV-234)

A mixture of carbamate 13 (OR-IV-211) (1.2 mg, 1.5 μmol), Cd—Pb couple (4.8 mg), aqueous $NH_4OAc$ solution (1 M, 50 μL), $H_2O$ (150 μL), and THF (150 μL) was stirred at 20° C. under $N_2$. After 1 hour an extra portion of Cd—Pb couple (1.2 mg) was added and the mixture was continued to stir for another 1 hour. The solvents were evaporated and $CHCl_3$ (5 mL) was added to the residue. The suspension was filtered through a sintered Buchner glass funnel and the solvent was concentrated. The crude residue was purified by prep-HPLC following the same procedure as in 13 (OR-IV-211) to give the product 15 (OR-IV-234) in the form of a salt with formic acid (0.57 mg, 59%). $^1$H NMR (500 MHz, $CDCl_3$) δ 8.41 (brs, 2H), 7.10 (s, 1H), 6.87 (d, J 11.9 Hz, 1H), 6.67 (t, J=11.6 Hz, 1H), 6.39 (d, J=15.8 Hz, 1H), 6.34-6.29 (m, 1H), 6.32 (d, J=15.9 Hz, 1H), 5.68 (t, J=7.5 Hz, 1H), 5.57 (d, J=8.9 Hz, 1H), 5.37 (d, J 11.6 Hz, 1H), 5.19-5.12 (m, 1H), 3.86-3.25 (brs, 4H), 3.64 (d, J=7.5 Hz, 2H), 3.20 (dd, J=14.6, 3.4 Hz, 1H), 3.15 (dd, J=14.6, 10.7 Hz, 1H), 3.07-3.01 (m, 1H), 2.92-2.89 (m, 1H), 2.77-2.72 (m, 1H), 2.63 (s, 6H), 2.63-2.59 (m, 1H), 2.52 (dd, J=17.5, 11.7 Hz, 1H), 2.32 (dd, J=13.0, 11.1 Hz, 1H), 2.12 (d, J=13.0 Hz, 1H), 2.10-2.07 (m, 1H), 2.02 (s, 3H), 1.99-1.96 (m, 1H), 1.86 (s, 3H), 1.83 (s, 3H), 1.27 (d, J=6.4 Hz, 3H). HRMS ($ESI^+$): Calcd. for $C_{30}H_{44}N_3O_4S$ ($[M+H]^+$), 542.3053. Found: 542.3044.

Example 2

Plasma Protein Binding Assay

In this example, the plasma protein binding assay used to provide the plasma protein binding data is described.

The assay includes the following steps.

1. Frozen plasma was thawed and centrifuged at 1120 g for 10 min to remove any particulates. The plasma was decanted, the pH was measured and, if required, was adjusted to pH7.4 with lactic acid.
2. All compounds were prepared at 10 mM concentration in DMSO. The solutions were carefully vortexed to ensure the compounds dissolved. The 10 mM DMSO solutions were diluted to 500 μM MeOH solutions (5+95 μl).
3. In a 2 mL 96-well plate (DWP), 1000 μL of plasma was pipetted into each well in Columns 1-4.
4. 10 μL of the 500 μM compound solution was pipetted to 1000 μL of corresponding plasma. (The final DMSO=0.05%). The solution was capped and carefully vortexed for 5 min.
5. 200 μL of PBS buffer was added to each receiver well of the dialysis plate (buffer was added to the Receiver first).
6. The bottom of dialysis plate was capped and turned over to the orange donor side (top) of dialysis plate.
7. The orange donor side of the dialysis plate was uncapped and 200 μL of the 10 μM drug/plasma samples were transferred from the 2 ml 96-DWP to the corresponding donor wells in the dialysis plate. The orange donor side of the dialysis plate was then capped.
8. The dialysis plate was placed onto the plate rotator in a 37° C. oven and incubated at 37° C. with a rotation speed 20 rpm for 22 hr.
9. To a 1 mL 96-DWP, 50 μL/well of the 5 μM drug/plasma samples was pipetted from the 2 mL 96-DWP in triplicate. 50 μL/well of PBS and then 300 μL of ACN/IS was added. The plate was kept at 4° C. This plate serves as the recovery plate.
10. Two 1 mL 96-DWP were prepared and marked as Donor Plate and Receiver Plate.
11. The dialysis plate was removed from the 37° C. oven.
12. The caps were removed from the donor side of the dialysis plate.
13. 50 μL of samples were pipetted from the donor side of the dialysis plate and added into the 96-DWP Donor Plate. 50 μL of PBS buffer was added into the 96-DWP Donor Plate.
14. The donor side of the dialysis plate was capped and turned over. Caps were removed from the Receiver side wells. 50 uL of samples were pipetted from the Receiver side of the dialysis plate and added to the 96-DWP Receiver Plate.
15. 50 μL of blank plasma was added into the 96-DWP Receiver Plate.
16. 300 μL/well of 1 μM of imipramine (IS) in acetonitrile (ACN) was added into the 96-DWP Donor Plate, the 96-DWP Receiver Plate, and the Recovery Plate.
17. The three plates were capped and vortexed for 10 minutes.
18. The plates were centrifuged at 4° C. at 4000 rpm for 10 min.
19. 150 μL of quench samples were transferred from each plate to a corresponding 96-DWP injection plate.
20. 150 μL of 0.1% acetic acid/water was added to the injection plates.
21. The injection plates were capped and vortexed for 5 min.
22. The plates were centrifuged at 4° C. at 4000 rpm for 5 min.
23. The samples in the Receiver Plate, Donor Plate, and Recovery Plate were analyzed by LC/MS/MS HPLC: Agilent 1290 infinity binary LC/HTC injector. Column: Sigma-Aldrich Supelco Ascentis fused-core C18, 2.7 um, 2.1×20 mm. Solvent A: 0.1% acetic acid/water.

Solvent B: 0.1% acetic acid/acetonitrile. Column temperature: 40° C. Injection volume: 2 uL. Time/flow rate: 0 min/0.5 mL/min 1.3 min/0.5 mL/min 1.31 min/1.0 mL/min|1.7 min/1.0 mL/min.

MS/MS: Agilent 6460, Positive, ESI. Sheath gas temperature: 400° C. Sheath gas flow: 12 L/min. Gas temperature: 300° C. Gas flow: 11 L/min. Capillary voltage: 4000 V. Nozzle voltage: 500 V. Nebulizer: 35 psi. Cell accelerator voltage: 7 V.

While the preferred embodiment of the invention has been illustrated and described, it will be appreciated that various changes can be made therein without departing from the spirit and scope of the invention.

The invention claimed is:

1. A compound having formula (I):

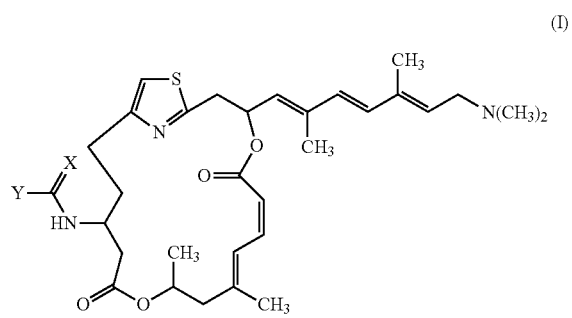

(I)

or a stereoisomer, a racemate, or a pharmaceutically acceptable salt thereof,
wherein
X is selected from O, NH, and S; and
Y is selected from R, $OR^1$, $SR^3$, and $N(R^1)R^2$,
wherein R is selected from C1-C6 alkyl, C1-C6 haloalkyl, C6-C10 aryl, and C3-C12 alkyl groups in which one or more carbons are replaced with O or N atoms, and
wherein $R^1$ and $R^2$ are independently selected from hydrogen, C1-C6 alkyl, C1-C6 haloalkyl, C6-C10 aryl, and C3-C12 alkyl groups in which one or more carbons are replaced with O or N atoms.

2. The compound of claim 1 having formula (II):

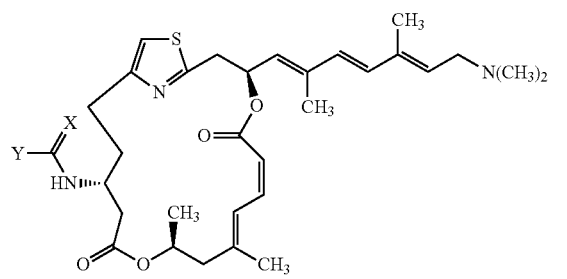

(II)

or a pharmaceutically acceptable salt thereof,
wherein
X is selected from O, NH, and S; and
Y is selected from R, $OR^1$, $SR^1$, and $N(R^1)R^2$,
wherein R is selected from C1-C6 alkyl, C1-C6 haloalkyl, C6-C10 aryl, and C3-C12 alkyl groups in which one or more carbons are replaced with O or N atoms, and
wherein $R^1$ and $R^2$ are independently selected from hydrogen, C1-C6 alkyl, C1-C6 haloalkyl, C6-C10 aryl, and C3-C12 alkyl groups in which one or more carbons are replaced with O or N atoms.

3. The compound of claim 1 having formula (III):

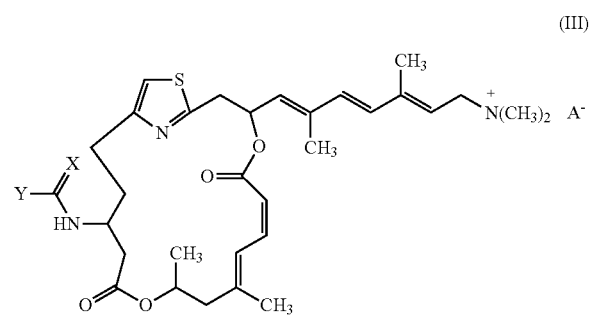

(III)

wherein $A^-$ is a pharmaceutically acceptable counter ion.

4. The compound of claim 2 having formula (IV):

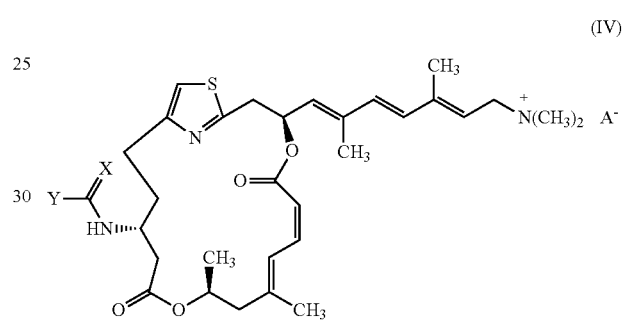

(IV)

wherein $A^-$ is a pharmaceutically acceptable counter ion.

5. The compound of claim 3, wherein $A^-$ is selected from the group consisting of chloride, bromide, iodide, sulfate, phosphate, formate, acetate, trifluoroacetate, maleate, fumarate, succinate, tartrate, oxalate, citrate, malate, benzoate, toluenesulfonate, methanesulfonate, and benzenesulfonate.

6. The compound of claim 1, wherein X is O and Y is R.

7. The compound of claim 1, wherein X is O and Y is $OR^1$.

8. The compound of claim 1, wherein X is O and Y is $N(R^1)R^2$.

9. The compound of claim 1, wherein X is O and Y is $SR^1$.

10. The compound of claim 1, wherein X is S and Y is R.

11. The compound of claim 1, wherein X is S and Y is $OR^1$.

12. The compound of claim 1, wherein X is S and Y is $N(R^1)R^2$.

13. The compound of claim 1, wherein X is S and Y is $SR^1$.

14. The compound of claim 1, wherein X is NH and Y is R.

15. The compound of claim 1, wherein X is NH and Y is $OR^1$.

16. The compound of claim 1, wherein X is NH and Y is $N(R^1)R^2$.

17. The compound of claim 1, wherein X is NH and Y is $SR^1$.

18. The compound of claim 1, wherein the C3-C12 alkyl group in which one or more carbons are replaced with O is selected from —CH$_2$—O—CH$_3$, —CH$_2$CH$_2$—O—CH$_3$, and -CH$_2$CH$_2$—O—CH$_2$CH$_2$—O—CH$_3$.

19. The compound of claim 1, wherein the C3-C12 alkyl group in which one or more carbons are replaced with N is selected from —CH$_2$—NH—CH$_3$, —CH$_2$—N(CH$_3$)$_2$, —CH$_2$CH$_2$—NH—CH$_3$, and —CH$_2$CH$_2$—N(CH$_3$)$_2$.

20. A compound having formula (V):

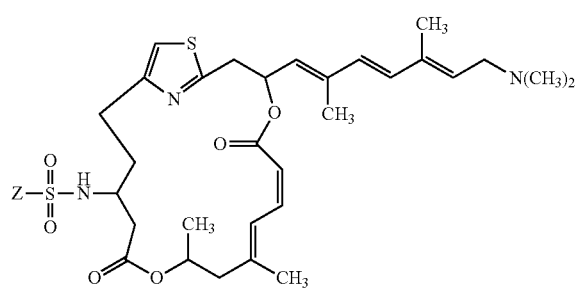

(V)

or a stereoisomer, a racemate, or a pharmaceutically acceptable salt thereof, wherein Z is selected from R and OR$^1$, wherein R is selected from C1-C6 alkyl, C1-C6 haloalkyl, C6-C10 aryl, and C3-C12 alkyl groups in which one or more carbons are replaced with O or N atoms, and wherein R$^1$ is selected from hydrogen, C1-C6 alkyl, C1-C6 haloalkyl, C6-C10 aryl, and C3-C12 alkyl groups in which one or more carbons are replaced with O or N atoms.

21. The compound of claim 20 having formula (VI):

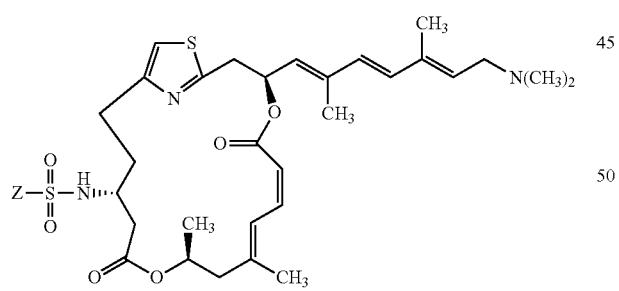

(VI)

or a pharmaceutically acceptable salt thereof, wherein

Z is selected from R and OR$^1$, wherein R is selected from C1-C6 alkyl, C1-C6 haloalkyl, C6-C10 aryl, and C3-C12 alkyl groups in which one or more carbons are replaced with O or N atoms, and wherein R$^1$ is selected from hydrogen, C1-C6 alkyl, C1-C6 haloalkyl, C6-C10 aryl, and C3-C12 alkyl groups in which one or more carbons are replaced with O or N atoms.

22. The compound of claim 20 having formula (VII):

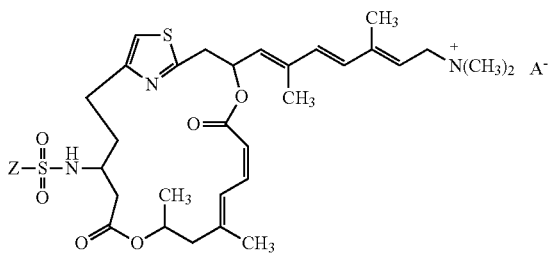

(VII)

wherein A$^-$ is a pharmaceutically acceptable counter ion.

23. The compound of claim 21 having formula (VIII):

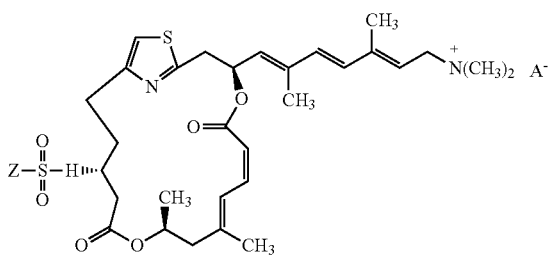

(VIII)

wherein A$^-$ is a pharmaceutically acceptable counter ion.

24. A compound having formula (IX):

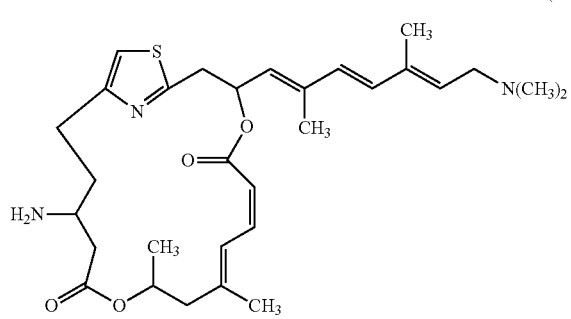

(IX)

or a stereoisomer, a racemate, or a pharmaceutically acceptable salt thereof.

25. The compound of claim 24 having formula (IX):

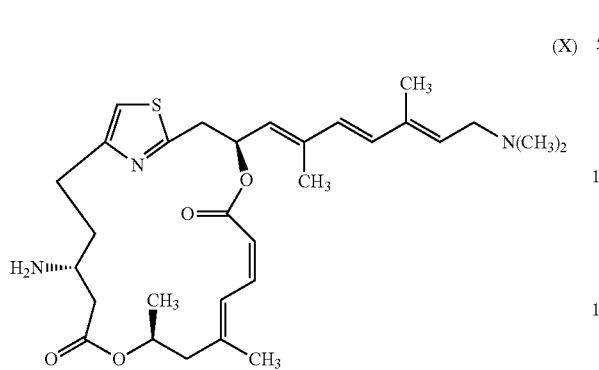

or a pharmaceutically acceptable salt thereof.

26. The compound of claim 24 having formula (XI):

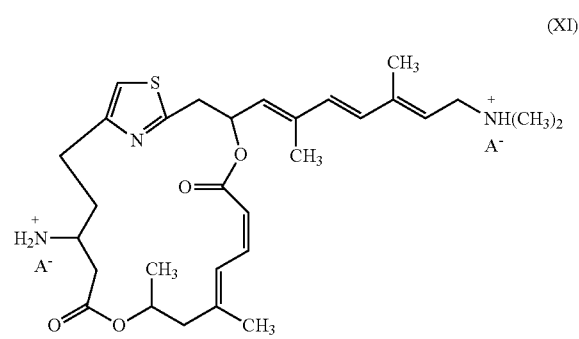

wherein $A^-$ is a pharmaceutically acceptable counter ion.

27. The compound of claim 24 having formula (XII):

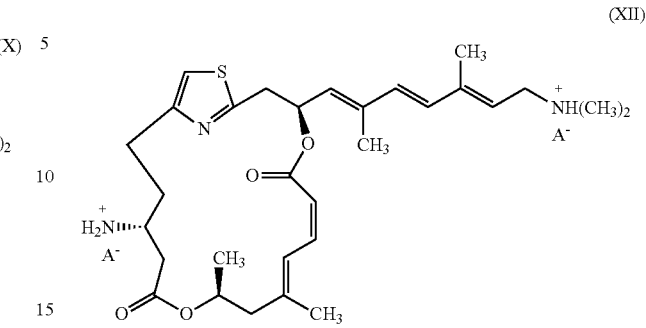

wherein $A^-$ is a pharmaceutically acceptable counter ion.

28. A pharmaceutical composition, comprising a compound of claim 24, or a stereoisomer, a racemate, or a pharmaceutically acceptable salt thereof, and a pharmaceutically acceptable carrier.

29. An antibody conjugate for the delivery of a β-amino pateamine derivative, comprising a compound of claim 24 covalently coupled directly or through a linker unit to an antibody or functional fragment thereof.

30. A pharmaceutical composition, comprising the antibody conjugate of claim 29 and a pharmaceutically acceptable carrier.

31. A method for inhibiting growth of chronic lymphocytic leukemia (CLL) cells, comprising contacting CLL cells with a compound of claim 24, or a stereoisomer, a racemate, or a pharmaceutically acceptable salt thereof.

32. A method for treating chronic lymphocytic leukemia (CLL), comprising administering to a subject in need thereof a therapeutically effective amount of a compound of claim 24, or a stereoisomer, a racemate, or a pharmaceutically acceptable salt thereof.

33. A method for inhibiting growth of chronic lymphocytic leukemia (CLL) cells, comprising contacting CLL cells with an antibody conjugate of claim 29.

34. A method for treating chronic lymphocytic leukemia (CLL), comprising administering to a subject in need thereof a therapeutically effective amount of an antibody conjugate of claim 29.

* * * * *

UNITED STATES PATENT AND TRADEMARK OFFICE
CERTIFICATE OF CORRECTION

Page 1 of 1

PATENT NO. : 10,889,596 B2
APPLICATION NO. : 16/090528
DATED : January 12, 2021
INVENTOR(S) : Romo et al.

It is certified that error appears in the above-identified patent and that said Letters Patent is hereby corrected as shown below:

In the Claims

| Column | Line | |
|---|---|---|
| 33 | 35 | change "$SR^3$" to -- $SR^1$ --. |

Signed and Sealed this
Thirtieth Day of August, 2022

Katherine Kelly Vidal
*Director of the United States Patent and Trademark Office*